United States Patent
Hagay et al.

(10) Patent No.: US 9,867,861 B2
(45) Date of Patent: Jan. 16, 2018

(54) PROCESS FOR THE LARGE SCALE PRODUCTION OF FRUIT CELLS AND TREATMENT OF DISEASES WITH SUCH CELLS

(71) Applicant: BIO HARVEST LTD, Rehovot (IL)

(72) Inventors: Yoheved Hagay, Rehovot (IL); Michal Abargel, Rishon Lezion (IL); Malkit Azachi, Rehovot (IL); Yoav Roth, Ashdod (IL); Rivka Yatuv, Shoham (IL)

(73) Assignee: BIO HARVEST LTD., Rehovot (IL)

( * ) Notice: Subject to any disclaimer, the term of this patent is extended or adjusted under 35 U.S.C. 154(b) by 15 days.

(21) Appl. No.: 14/655,052

(22) PCT Filed: Dec. 24, 2013

(86) PCT No.: PCT/IL2013/051052
§ 371 (c)(1),
(2) Date: Jun. 24, 2015

(87) PCT Pub. No.: WO2014/102776
PCT Pub. Date: Jul. 3, 2014

(65) Prior Publication Data
US 2016/0193274 A1  Jul. 7, 2016

Related U.S. Application Data

(60) Provisional application No. 61/745,843, filed on Dec. 26, 2012, provisional application No. 61/764,547, (Continued)

(51) Int. Cl.
*A61K 36/87* (2006.01)
*C12N 5/04* (2006.01)

(52) U.S. Cl.
CPC ............. *A61K 36/87* (2013.01); *C12N 5/04* (2013.01)

(58) Field of Classification Search
CPC ....................................... A61K 36/00
See application file for complete search history.

(56) References Cited

U.S. PATENT DOCUMENTS 8,216,801 B2    7/2012  Eshdat et al.
2008/0160560 A1*  7/2008  Ho ........................ C12N 5/04
                                                       435/29

FOREIGN PATENT DOCUMENTS

CN    102191214    9/2011
CN    102218049    10/2011
(Continued)

OTHER PUBLICATIONS

Hirasuna et al, Enhanced anthocyanin production in grape cell cultures. Plant Science (Limerick) (1991), vol. 78, No. 1, pp. 107-120.*

(Continued)

*Primary Examiner* — Qiuwen Mi
(74) *Attorney, Agent, or Firm* — Pearl Cohen Zedek Latzer Baratz LLP

(57) ABSTRACT

The disclosure provides a method for treating, reducing, alleviating or preventing metabolic syndrome or metabolic malady, comprising administering a composition comprising a cell line callus culture of fruit cells grown in vitro. Further provided are fruit cells prepared according to a large scale process. The cell line callus culture of grape berry cells manufactured according to the process includes resveratrol in an amount of at least 1000 mg/kg powder.

19 Claims, 9 Drawing Sheets

Related U.S. Application Data filed on Feb. 14, 2013, provisional application No. 61/878,652, filed on Sep. 17, 2013.

(56) References Cited

FOREIGN PATENT DOCUMENTS

| CN | 102382862 | 3/2012 |
|---|---|---|
| WO | WO2006/090388 | 8/2006 |
| WO | WO-2006/090388 | 8/2006 |
| WO | WO-2008/135991 | 11/2008 |
| WO | WO-2014/068557 | 5/2014 |

OTHER PUBLICATIONS

Liu et al, Effect of grape genotype and tissue type on callus growth and production of resveratrols and their piceids after UV-C irradiation. Food chemistry (2010), vol. 122, No. 3, pp. 475-481.*

Sarfaraz Sadruddin et al: "Resveratrol Biologic and Therapeutic Implications" Journal of the Cardiometabolic Syndrome, vol. 4, No. 2, Mar. 1, 2009, pp. 102-106, XP0552747396, ISSN: 1559-4564, DOI: 10.1111/j.1559-4572.2008.00039.x.

Krisa S et al: "Obtaining Vitis vinifera cell cultures producing higher amounts of malvidin-3-0-[beta]-glucoside" Biotechnology Letters, Springer Netherlands, NL, vol. 21 No. 6, Jan. 1, 1999, pp. 497-500, XP002583527, ISSN: 0141-5492.

Kaniti Panday: "Plant polyphenols dietary antioxidants in human health and disease" Oxidative Medicine and Cellular Longevity, vol. 2 No. 5, Nov. 1, 2005, pp. 270-278, XP55121781.

Stintzing F C et al: "Functional properties of anthocyanins and betalains in plants, food, and in human nutrition" Trends in Food Science and Technology, Elsevier Science Publishers, GB, vol. 15, No. 1, Jan. 1, 2004, pp. 19-38, XP004481862, ISSN: 0924-2244, DOI: 10.1016/J. TIFS.2003.07.004.

Supplementary European Search Report for Application No. 13866675.5 dated Jun. 2, 2016.

PCT Search Report for App. No. PCT/IL2013/051052 dated May 8, 2014.

Satoh et al "Purified Eicosapentaenoic Acid Reduces Small Dense LDL, Remnant Lipoprotein Particles, and C-Reactive Protein in Metabolic Syndrome" Diabetes Care vol. 30, No. 1 Jan. 2007, pp. 144-146.

Seymour et al. "Whole Grape Intake Impacts Cardiac Peroxisome Proliferator-Activated Receptor and Nuclear Factor κB Activity and Cytokine Expression in Rats With Diastolic Dysfunction." Hypertension 2010;55: Mar. 15, 2010, pp. 1179-1185.

Office Action of Chinese Patent Application No. 201380073592.3 dated Mar. 3, 2017.

Office Action of European Patent Application No. 13 866 675.5 dated Aug. 11, 2017.

Leibowitz et al., "Red grape berry-cultured cells reduce blood pressure in rats with metabolic-like syndrome", Eur. J. Nutr., Oct. 26, 2013, vol. 53, pp. 973-980.

Pandey et al. "Plant polyphenols as dietary antioxidants in human health and disease", Oxid. Med. Cell. Longev., Nov. 2009, vol. 2 No. 5, pp. 270-278.

Seymour et al. "Whole Grape Intake Impacts Cardiac Peroxisome Proliferator-Activated Receptor and Nuclear Factor κB Activity and Cytokine Expression in Rats with Diastolic Dysfunction", Hypertension, Mar. 2010, vol. 55, pp. 1179-1185.

Sadruddin et al. "Resveratrol: Biologic and Therapeutic Implications", J. CardioMetab. Syndr., Mar. 2009, vol. 4, No. 2, pp. 102-106.

Lasa et al. "Delipidating effect of resveratrol metabolites in 3T3-L1 adipocytes", Mol. Nutr. Food Res., Sep. 2012, vol. 56, pp. 1559-1568.

"Pharmacokinetics of Resveratrol Comprising Products", Dec. 9, 2012, url: https://clinicaltrials.gov/ct2/show/NCT01747252.

Shen et al. "Stimulation of trans-resveratrol biosynthesis in Vitis vinifera cv. Kyoho cell suspension cultures by 2, 3-dihydroxypropyl jasmonate elicitation" Plant Biotechnol., Sep. 2012, vol. 15, No. 5, ISSN: 0717-3458.

Chen et al. Resveratrol enhances insulin secretion by blocking $K_{ATP}$ and $K_V$ channels of beta cells, Eur. J. Pharmacol., Jul. 2007, vol. 568, pp. 269-277.

\* cited by examiner

US 9,867,861 B2

PROCESS FOR THE LARGE SCALE PRODUCTION OF FRUIT CELLS AND TREATMENT OF DISEASES WITH SUCH CELLS

CROSS-REFERENCE TO RELATED APPLICATIONS

This application is a National Phase Application of PCT International Application No. PCT/IL2013/051052, International Filing Date Dec. 24, 2013, claiming the benefit of U.S. Provisional Patent Applications Nos. 61/745,843, filed Dec. 26, 2012, and 61/878,652, filed Sep. 17, 2013, and 61/764,547 filed Feb. 14, 2013, which are all hereby incorporated by reference.

FIELD OF THE INVENTION

This invention is directed to a process for the large scale production of fruit cells. One embodiment of the invention is directed to a process for the large scale in vitro production of fruit cells, which include primary and secondary metabolites. This invention is further directed to methods of treating, preventing, alleviating and/or reducing one or more condition or complication associated with metabolic syndrome by administration of a cell line callus culture of fruit cells.

BACKGROUND OF THE INVENTION

Large scale processes are known in the art and are necessary for the industrial production of various materials. Since large scale processes cannot be performed by the same means as small scale processes, specific processes for the large scale production of materials must be designed, even if small scale processes exist.

Nutraceuticals are sometimes prepared using synthetic processes that provide the desired active ingredients, e.g., polyphenols, which are naturally found in fruit cells. However, the use of synthetic processes does not provide the natural ingredients along with the active ingredients, which sometimes contribute to the efficiency of the formulation.

Other types of nutraceuticals are prepared from the natural plants; however, all known large scale processes for preparing nutraceuticals from plants include the extraction of the prepared plant cells in order to obtain the desired active ingredient. However, when plants containing polyphenols, for example, are extracted, the amount of polyphenols, including resveratrol, may be very high in the extraction and therefore, the final product may be bitter. Also, only certain parts of the plant may be successfully extracted since only they contain the desired amounts of the active ingredients.

Small scale processes for the preparation of fruit cells are known in the art; however, large scale processes are more difficult to design since they tend to amplify the production of the primary metabolites, while minimizing the productions of the secondary metabolites. Since active ingredients, such as polyphenols, are secondary metabolites their production in large-scale processes is complex.

Thus, there is a need in the art for a large scale process for preparing fruit cells from natural ingredients, which includes the production of both the primary and the secondary metabolites of the fruit cells.

Metabolic abnormalities are associated with obesity, insulin resistance glucose intolerance, type II diabetes mellitus (DMII), dyslipidemia fatty liver, steatohepatitis, steatosis. These abnormalities increase the risk of stroke cardiovascular diseases. The etiology of the metabolic syndrome is considered to be multifactorial involving genetic and environmental effects.

Atherosclerosis is a disease of the vascular bed caused by fatty deposit build up in blood vessel walls that narrow the passageway for blood flow within blood vessels. This process may affect all arteries particularly the coronary arteries and may lead to eventual blockage of the coronary arteries resulting in a heart attack, which is the leading cause for premature death in the United States.

Fatty liver disease encompasses a spectrum of clinical conditions characterized histologically mainly by macrovesicular steatosis of the liver. The histopathological spectrum of fatty liver disease ranges from the simple fatty liver (steatosis) to the steatohepatitis, a variant, which has variable degrees of fibrosis. Steatohepatitis may be progressive and can lead to cirrhosis, liver failure and hepatocellular carcinoma and may be a major cause of cryptogenic cirrhosis. The common risk factors for fatty liver disease are obesity, type II diabetes, and hyperlipidemia.

Type II diabetes is among the most common chronic human diseases, affecting almost 8% of the adult population and 19% of people above the age of 65 years in the United States.

Metabolic syndrome also known as "the deadly quartet" or "Syndrome X" or the "Insulin Resistance Syndrome" is a cluster of risk factors for various diseases, such as cardiovascular diseases, stroke and diabetes mellitus type II, i.e. insulin resistance, hyperinsulinemia, abdominal obesity, (caused by an accumulation of intra-abdominal fat), elevated serum lipids, and high blood pressure. 25% of adults living in the United States are diagnosed with metabolic syndrome. It is believed that the pathophysiology of the metabolic syndrome is related to insulin resistance. The risk factors include the following: elevated waist circumference (≥102 cm in man and 88 cm in women); elevated triglycerides (>150 mg/dL); reduced high-density lipoprotein (HDL) cholesterol (<40 mg/dL in men and 50 mg/dL in women); elevated blood pressure (>130/85 mm Hg) and elevated fasting glucose (>100 mg/dL. Other risk factors may contribute to the metabolic syndrome as well. Additionally, the risk factors may vary in different populations.

Impaired Fasting Glycaemia (IFG) is a pre-diabetic state of dysglycemia associated with insulin resistance, defined as a fasting glucose level of 101-126 mg/dL.

Impaired Glucose Tolerance (IGT) is a pre-diabetic state of dysglycemia associated with insulin resistance defined with similar definition as for IFG or alternatively, defined as a glucose level of 141 to 199 mg/dL two hours following oral consumption of a high glucose meal, typically 75 grams of glucose.

Many of the metabolic maladies are characterized by triglyceride accumulation and insulin resistance.

Triglyceride accumulation in various body tissues, such as muscle, liver and pancreas tissue is considered to be an important factor for organ specific insulin resistance leading to the development of a metabolic malady. Furthermore, accumulation of lipid droplets, which is identical to the term lipid bodies in tissues occurs early in the development of insulin resistance and is correlated with its severity.

Persistent hypertension is one of the risk factors for several diseases and disorders. Hypertension is the single most important modifiable risk factor for ischemic stroke, the third leading cause of death in the Western world. Risk of stroke begins to increase at blood pressure (BP) readings higher than 120/80 millimeters of mercury (mm Hg). Most estimates for hypertension indicate a relative risk of stroke of approximately 4 when hypertension is defined as systolic blood pressure (SBP) ≥160 mm Hg and/or diastolic blood pressure (DSP) ≥95 mm Hg.

Community-based studies have demonstrated that hypertension may contribute to the development of heart failure in as many as 50-60% of patients. In patients with hypertension, the risk of heart failure is increased by 2-fold in men and by 3-fold in women. According to the Framingham Study, hypertension accounts for about one quarter of heart failure cases.

Hypertension is not only a well-established cardiovascular risk factor but also increases the risk of atherosclerosis. Clinical trials have shown that, in the highest quintile of DBP, even with the added risks of high cholesterol and smoking, hypertension still contributes significantly to risk for atherosclerosis.

Hypertension has been reported to occur in 85% to 95% of patients with chronic kidney disease (CKD). Uncontrolled hypertension is a risk factor for developing CKD, and is the second leading cause of end-stage renal disease in the USA.

In the past, most attention was paid to DBP; but nowadays it is recognized that both high SBP and high pulse pressure (the numerical difference between SBP and DBP) are also risk factors. Importantly, it has been demonstrated that the combined evaluation of SBP and DBP improves cardiovascular risk prediction over the 2 individual components. Nevertheless, DBP is still an important cardiovascular risk factor. Isolated diastolic hypertension was a cardiovascular risk factor in the study by Franklin et al. Subjects with isolated diastolic hypertension represented 14% of the hypertensive population, and their cardiovascular risk was found to be about twice that of the subjects with normal BP (Schillaci et al., 2009). Moreover, a nationwide Chinese database also confirmed that isolated diastolic hypertension is an independent risk factor for cardiovascular disease.).

Lipid peroxidation refers to the oxidative deterioration of lipids in a process resulting in cell damage. Lipid peroxidation may be one mechanism through which several risk factors may promote cardiovascular disease.

Lipid peroxidation was found to be highly correlated with cardiovascular risk factors such as age, triglycerides, smoking, cholesterol High-density lipoprotein (HDL) and body mass index (BMI).

Pregnant, oophorectomized, and post-menopausal women exhibit higher levels of lipid peroxidation than non-pregnant, non-oophorectomized and pre-menopausal women, and high level of lipid peroxidation during these states is responsible, at least in part, for their increased risk of CVD.

Low density lipoprotein (LDL) isolated from patients with essential hypertension exhibits increased propensity for oxidation. Thus, oxidized LDL (Ox-LDL) may predispose to accelerated atherosclerosis, and the propensity of LDL for lipid peroxidation may be a risk factor for atherogenesis as important as the plasma concentration of LDL itself.

Flow-mediated dilation (FMD) as an expression of endothelial dysfunction may serve as an indicator of several diseases. FMD was highly predictive for coronary artery disease (CAD) with an odds ratio of 1.32 for each percent decrease in FMD (p=0.001). Not only in atherosclerosis but also in systemic sclerosis FMD was highly correlated with the progression of the disease. There was an inverse correlation between FMD values and disease duration.

In post-menopausal women low FMD values were correlated with an increase in relative risk to developing hypertension.

FMD is associated with increased mortality risk in ischaemic advanced chronic heart failure (ACHF) patients. (Shechter et al., 2009). Moreover, persistent low FMD despite therapies for heart failure (HF) and atherosclerotic risk factors was a predictor of cardiac events in patients with chronic ischemic HF.

Stroke patients had significantly lower flow-mediated dilation (FMD) values than nonstroke patients. FMD as an independent predictor of cryptogenic stroke when adjusted by age, sex, and presence of patent foramen ovale (PFO).

Finally, in children with heterozygous familial hypercholesterolemia (heFH) who are prone to premature atherosclerosis decreased FMD is detected before structural atherosclerotic changes occur.

Nutraceuticals derived from polyphenol-containing fruit extracts are known for their beneficial effects. The use of red wine as a source of these regulatory constituents is limited due to its high alcoholic content and sugar. In addition, it has been shown that the therapeutic effect of wine and wine grapes is dependant on species, location, year (annual climate), processing etc. and therefore reliance on red wine, grapes or grape seeds as a source of these regulatory compounds does not lead to a homogeneous or consistent supply of material. Furthermore, fruits are often contaminated by residual fungicides, pathogens, pesticides and pollutants.

Moreover, the potential benefit of gastrointestinal delivery of polyphenols from red wines and fruit extracts is limited by its bioavailability to target tissues and cells. Due to marked differences in their bioavailability while passing through the intestines, no correlation can be drawn between the abundance of a certain polyphenol in a given food and its concentration as an active compound in vivo. Absorbance of flavonoids in the small intestines, for example, ranges from 0-60% of the dose, and elimination half-lives range from 2-48 hours. Most polyphenols undergo extensive metabolism in the intestine, and are present in serum and urine predominantly as glucuronides, methyl or sulfate. Among the known polyphenols, the phytoalexin resveratrol (trans-3,5,4'-trihydroxystilbene) (RES), found in red grapes, red wine and other foods such as different kind of berries and peanuts has drawn most of the attention. It is believed to be responsible for the "French paradox", a phenomenon associated with low incidence of cardiovascular diseases despite high-fat diet as a result of moderate red wine consumption. However, RES bioavailability is compromised by its physicochemical properties such as low water solubility and also its high hepatic uptake. Moreover, oral bioavailability of RES is extremely low due to rapid and extensive metabolism with the consequent formation of various metabolites.

Studies investigating RES activity and effects rely mainly on three sources of resveratrol, namely pure synthetic RES, natural plant-derived RES (e.g. *Poligonum cupcidatum* extracts) products, or to a lesser extent whole red grapes or their products (red wine, grape juice, grape extracts). Red Grape Cells (RGC; Fruitura Bioscience Ltd, Israel) is a natural patent-protected formulation of cultured cells originated from the fruits of *Vitis Vinifera* L. cultivar comprising the whole matrix of polyphenols including resveratrol and other ingredients naturally existing in red grape.

There is thus a need for natural (phyto) compositions that may be prepared in a large scale process in which the amount of the active ingredient is consistent and recurrent (e.g., clonal preparations), is highly bioavailable and easily administered for the treatment of various disorders, including conditions or complication associated with metabolic disorder or metabolic maladies.

SUMMARY OF THE INVENTION

In an embodiment of the invention, there is provided a method for treating, reducing, alleviating or preventing metabolic syndrome or metabolic malady, comprising administering a composition comprising a cell line callus culture of fruit cells grown in vitro.

According to some embodiments, the invention provides a method for the treatment of one or more conditions selected from the group consisting of coronary heart disease (atherosclerosis), blood pressure, ischemic, heart failure, atherosclerosis, chronic kidney disease (CKD) and renal disease system sclerosis, chronic heart failure, hypertension, diabetes, hyperlipidemia, impaired glucose tolerance, hepatic steatosis, hyperglycemia, pre-diabetic state, new onset diabetes, Insulin resistance, Diabetes Mellitus, Impaired Fasting Glucose, hypertriglyceridemia, anti-inflammation (adiponectin), hypercholesterolemia, low HDL levels, fatty liver and obesity, in a subject, comprising the steps of: administering to said subject a composition comprising a cell line callus culture of fruit cells grown in vitro. In some embodiments the subject is diagnosed as having a metabolic syndrome.

According to some embodiments, the cell line callus culture of fruit cells is prepared according to a large scale process comprising: growing fruit cells in a flask; inoculating the fruit cells from the flask into a first bioreactor; inoculating the fruit cells from the first bioreactor into another bioreactor, wherein the another bioreactor is a last bioreactor or an intermediate bioreactor and wherein at least one of the first and the another bioreactor is disposable; and harvesting the fruit cells from the last bioreactor;
wherein the fruit cells harvested from the last bioreactor are dried.

According to some embodiments, a Gamborg B5 medium enriched with magnesium, phosphate or nitrate salts or a combination thereof is used.

In some embodiments, the disposable bioreactor is made from one or more layers of polyethylene. In some embodiments, the wherein the disposable bioreactor is made from an inner and outer layer of polyethylene and a middle nylon layer.

In some embodiments, there is provided a method for treating, reducing, alleviating or preventing metabolic syndrome or metabolic malady, comprising administering a composition comprising a cell line callus culture of fruit cells prepared according to a large scale process comprising: growing fruit cells in a flask;
inoculating the fruit cells from the flask into a first bioreactor;
inoculating the fruit cells from the first bioreactor into another bioreactor, wherein the another bioreactor is a last bioreactor or an intermediate bioreactor and wherein at least one of the first and the another bioreactor is disposable; and harvesting the fruit cells from the last bioreactor;
wherein the fruit cells harvested from the last bioreactor are dried.

In some embodiments, there is provided a method for treating, reducing, alleviating or preventing inflammation, comprising administering a composition comprising a cell line callus culture of fruit cells prepared according to a large scale process comprising: growing fruit cells in a flask;
inoculating the fruit cells from the flask into a first bioreactor;
inoculating the fruit cells from the first bioreactor into another bioreactor, wherein the another bioreactor is a last bioreactor or an intermediate bioreactor and wherein at least one of the first and the another bioreactor is disposable; and harvesting the fruit cells from the last bioreactor;
wherein the fruit cells harvested from the last bioreactor are dried.

The composition in some embodiments, may be administered once a day.

In some embodiments, a composition in a form of a powder comprising a cell line callus culture of grape berry cells grown in vitro in a large scale up process, whereby the cell line callus culture of grape berry cells is derived from one or more of grape-berry cross section, grape-berry skin, grape-berry flesh, grape seed, grape embryo of seeded or seedless cultivars or grape seed coat; wherein the cell line callus culture of grape berry cells includes resveratrol in an amount of at least 1000 mg/kg powder.

The composition is some embodiments is characterized by two peaks of concentration of resveratrol in the plasma following a single administration of the composition.

In some embodiments, there is provided a method of decreasing diastolic and systolic blood pressure at rest and/or during exercising and/or the resting heart rate comprising the step of administering to said subject a composition comprising a cell line callus culture of fruit cells grown in vitro.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

FIGS. 9A and 9B present the plasma contents of trans-RES after the administration of single dose of RGC RES, wherein FIG. 9A presents the total trans-RES and FIG. 9B presents free trans-RES. The presented values are means (n=15).

DETAILED EMBODIMENTS OF THE INVENTION

Figure 1:
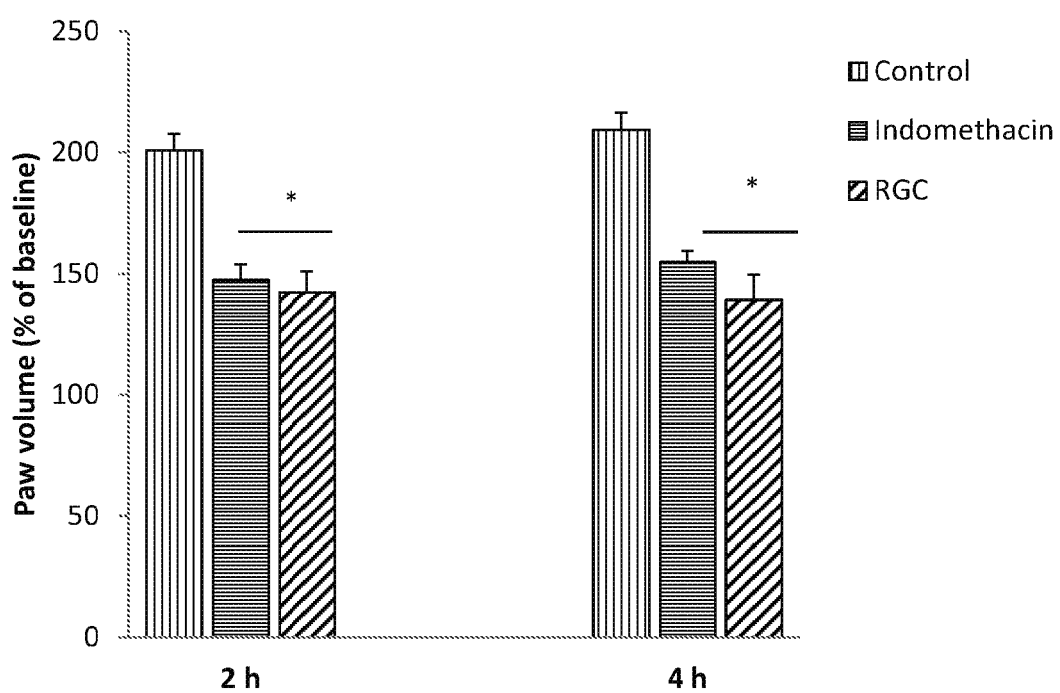
FIG. 1 demonstrates measurements of paw edema (volume %) in rates treated with RGC preparation, indomethacin and water as a control before carrageenan injection. Statistical analysis was carried out using two-way ANOVA for repeated measures, followed by Bonferroni post hoc tests. Comparison of control group (1M) to positive control group (2M) showed statistically significant difference at 2 and 4 h ($p<0.001$). Comparison of control group to RGC-preparation (3M) group showed statistically significant difference at 2 and 4 hours ($p<0.001$).

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

Embodiments of the invention are directed to methods of treating, reducing, alleviating and/or preventing metabolic syndrome or any condition or complication associated with metabolic syndrome such as, hypertension, diabetes, hyperlipidemia, impaired glucose tolerance, hepatic steatosis, hyperglycemia, pre-diabetic state, new onset diabetes, insulin resistance, Diabetes Mellitus, Impaired Fasting Glucose, hypertriglyceridemia, hypercholesterolemia, low HDL levels, fatty liver or obesity, comprising administering a composition comprising a cell line callus culture of fruit cells grown in vitro. In some embodiments of the invention, the cells are grown in a large scale process described below.

As used herein, the phrase "fruit cell culture" refers to a cell line callus culture of fruit cells grown in vitro in a large scale process. The fruit cell culture may be a single cell fruit culture (as used herein fruit cell-line culture or clonal culture) or a heterogeneous cell culture which comprises a number of cells derived from fruits having different genotypes (e.g., different varieties) or a number of cell types or tissues derived from a single fruit. The cell cultures of the present invention may be derived from any part of the fruit e.g. fruit skin, fruit flesh, seed coat and seed flesh.

As used herein the term "treating" refers to the prevention of some or all of the symptoms associated with a disease, a condition or disorder. The term "treating" also refers to alleviating, ameliorating or reducing the symptoms or underlying cause of the disease, prolongation of life expectancy of patients having a disease, preventing the disease, as well as complete recovery from a disease.

The words "treat" or "treatment" may further refer to a treatment wherein the object is to slow down (lessen) an undesired physiological change or disorder. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment.

The words "prevent" and "prevention" refer to prophylactic or preventative measures for protecting or precluding an individual not having a given condition from progressing to that condition. Individuals in which prevention is required include those who are prone or predisposed to a condition.

As used herein the phrase "inflammatory disorder" includes but is not limited to chronic inflammatory diseases and disorders and acute inflammatory diseases and disorders. This is exemplified in Example 4 which shows that the paw edema and behavioral hyperalgesia associated with carrageenan-induced hind paw inflammation in rats were positively attenuated by the oral administration of red grape cells (RGC) manufactured according to the large scale process described herein being indicative of the anti-inflammatory effect RGC that are prepared in a large scale process. In contrast, Gentilli et al (2001) describes that high concentration of resveratrol (50 mg/kg body weight) administered to rats prior to carrageenan injection into the paw failed to reduce paw edema. As used herein, the term "fatty liver" refers to a condition where fat accumulates excessively in liver cells due to the disorder of lipid metabolism. It may cause various diseases such as angina, myocardial infarction, stroke, arteriosclerosis and pancreatitis.

"Impaired glucose tolerance" is defined here on the basis of American Diabetes Association criteria. Impaired glucose tolerance is two-hour 75-g oral glucose tolerance test values of 140 to 199 mg per dL (7.8 to 11.0 mmol/l).

"Impaired fasting glucose" is defined here on the basis of American Diabetes Association criteria. Impaired fasting glucose is defined as fasting plasma glucose values of 100 to 125 mg per dL (5.6 to 6.9 mmol/l).

"Diabetes Mellitus" generally refers to fasting plasma glucose values of equal or greater than 126 mg/dL (7.0 mmol/l).

"Insulin resistance" is defined here as a fasting blood insulin level greater than 20 mcU/mL.

"New onset diabetes" (usually defined on the basis of a fasting blood glucose concentration of 7.0 mmol/l or more) in an individual.

A "pre-diabetic state" is a condition often preceding new onset diabetes and may be characterized by metabolic syndrome, impaired glucose tolerance, impaired fasting glucose or insulin resistance.

"Metabolic syndrome" or "syndrome X" is defined here on the basis of NCEP ATP III criteria, which are the presence of three or more of the following factors: 1) increased waist circumference (>102 cm [>40 in] for men, >88 cm [>35 in] for women); 2) elevated triglycerides (>150 mg/dl); 3) low HDL cholesterol (<40 mg/dl in men, <50 mg/dl in women); 4) non-optimal blood pressure (>130 mmHg systolic or mmHg diastolic); and 5) impaired fasting glucose (>110 mg/dl).

"Hyperglycemia" is a fasting blood glucose concentration of 7.0 mmol/l or greater.

"Hepatic steatosis" refers to a process describing the abnormal retention of lipids within a hepatocyle. Steatosis may result from obesity, insulin resistance, alcoholism or viral infection.

Embodiments of the invention are directed to methods of treating, reducing, alleviating and/or preventing metabolic syndrome or metabolic malady or any condition or complication associated with metabolic syndrome such as, hypertension, diabetes, hyperlipidemia, impaired glucose tolerance, Hepatic steatosis, hyperglycemia, pre-diabetic state, New onset diabetes, Insulin resistance, Diabetes Mellitus, Impaired fasting glucose, hypertriglyceridemia, hypercholesterolemia, low HDL levels, fatty liver or obesity, comprising administering a composition consisting essentially of a cell line callus culture of fruit cells grown in vitro.

In an embodiment of the invention, there is provided a method of treating an inflammatory disorder by administering to a subject in need a pharmaceutical or nutraceutical composition or a food additive comprising the grape cells cell culture manufactured large scale process in accordance with the embodiments of the invention.

According to some embodiments, the cell line callus culture of fruit cells is a cell line callus culture of grape berry cells. According to some embodiments, the cell line callus culture of grape berry cells is derived from one or more of grape-berry cross section, grape-berry skin, grape-berry flesh, grape seed, grape embryo of seeded or seedless cultivars or grape seed coat.

According to some embodiments, there is provided a method for lowering blood pressure in a subject comprising the step of administering to said subject a composition comprising a cell line callus culture of fruit cells grown in vitro. The subject may be a healthy subject. In some embodiments, the subject is a fit healthy subject that is engaged in a sports activity at least 3 times a week for at least half an hour.

According to some embodiments, the term "lowering blood pressure" refers to decreasing diastolic and systolic blood pressure in rest and/or during exercising and/or decreasing the resting heart rate comprising the step of administering to said subject a composition comprising a cell line callus culture of fruit cells grown in vitro.

This is exemplified in example 8 and in tables 18-19, which show the effect of a six week supplementation of RGC in healthy moderately trained cyclists which shows a significant decrease in resting diastolic blood pressure and peak diastolic blood pressure after exercising. RGC also caused a decrease in the systolic blood pressure at rest and in the heart rate at rest compared to the placebo group.

According to some embodiments, the composition is a nutraceutical composition. According to some embodiments, the composition is a pharmaceutical composition. According to some embodiments, the composition is a food additive. According to yet another embodiment, the nutraceutical composition further comprises a nutraceutical acceptable carrier. According to yet another embodiment, the pharmaceutical composition further comprises a pharmaceutical acceptable carrier. According to yet another embodiment, the composition further comprises a food additive acceptable carrier.

As used herein, the phrase "pharmaceutical composition" refers to a preparation of one or more, or of a mixture, of the active ingredients described herein (i.e., fruit cell culture as further described herein below) with other chemical components such as physiologically suitable carriers and excipients. The purpose of a pharmaceutical composition is to facilitate administration of a compound to an organism. According to some embodiments of the invention, since the active ingredient is derived from fruits (e.g. grapes), pharmaceutical composition as used herein is a nutraceutical composition and/or a food additive. The phrase "food additive", defined by the FDA in 21 C.F.R. 170.3(e)(1), includes any liquid or solid material intended to be added to a food product. This material can, for example, include an agent having a distinct taste and/or flavor or a physiological effect (e.g., vitamins). In addition the fruit cell cultures and preparations derived therefrom may be provided to animals as feed additives.

Herein the term "active ingredient" refers to the fruit cell culture accountable for the therapeutic effect. The therapeutic effect of the fruit cell culture of may be derived from an amount of active agents (e.g. polyphenols) comprised within or a particular combination or ratio of active agents comprised within the fruit cell cultures.

According to further embodiments, the cell line callus culture grown in vitro is dried.

According to some embodiments, the cell line callus culture comprises at least 0.5% polyphenols. According to further embodiments, the cell line callus culture comprises at least 2% polyphenols. The polyphenol content may be determined using methods known in the art, such as the spectrophotometric Folin-Ciocalteau test and HPLC analysis.

As used herein the term "polyphenols" refers to naturally occurring phyto organic compounds having more than one phenol group. Polyphenols may range from simple molecules, such as phenolic acid, to large, highly polymerized, compounds such as tannins. The phenolic rings of polyphenols are typically conjugated to various sugar molecules, organic acids and/or lipids. Differences in this conjugated chemical structure account for the chemical classification and variation in the modes of action and health properties of the various polyphenol compounds. Examples of polyphenols include, but are not limited to, anthocyanins, bioflavonoids (including the subclasses flavones, flavonols, isoflavones, flavanols, and flavanones), proanthocyanins, xanthones, phenolic acids, stilbenes and lignans. Resveratrol (3,4,5-trihydroxystilbene), which is one type of the polyphenols is a polyphenolic stilbene appears in its monomers forms; trans-resveratrol, cis-resveratrol, trans-glucoside and cis-glucoside.

Examples of fruits that contain polyphenols include, but are not limited to, grape, apple, blueberry, prune, cranberry, elderberry, bilberry, gentain, orange, mango, kiwi, pomegranate, blackberry, raspberry, strawberry, pear, cherry, plums tomato, grapefruit, pineapple, persimmon, red current and evodia fruit.

According to an embodiment of the invention, the fruit is a grape. The grape may be a colored grape (e.g. red, black, purple, blue and all color variations between). Alternatively, the grape may be a non-colored grape (e.g. green or white or any color variation between).

The fruit of this aspect of the invention may be of a wild or cultivated variety. Examples of cultivated grapes include those grapes belonging to the *vitis* genus. Examples of *vitis* varieties include, but are not limited to, *Vitis vinifera* (*V. vinifera*), *V. silvestris*, *V. muscadinia*, *V. rotundifolia*, *V. riparia*, *V. shuttleworthii*, *V. lubrisca*, *V. daviddi*, *V. amurensis*, *V. romanelli*, *V. aestivalis*, *V. Cynthiana*, *V. cineria*, *V. palmate*, *V. munsoniana*, *V. cordifolia*, Hybrid A23-7-71, *V. acerifolia*, *V. treleasei* and *V. betulifolia*.

According to some embodiments, the fruit cells or cell line callus culture are derived from a colored or a non-colored grape. As described herein, according to some embodiments, the fruit cells are prepared from a fruit cell culture. According to some embodiments of the invention, the fruit cells are prepared from a culture of grape berry cells. According to some embodiments, the culture of grape berry cells is derived from one or more of grape-berry cross section, grape-berry skin, grape-berry flesh, grape seed, grape embryo of seeded or seedless cultivars or grape seed coat. According to another embodiment, the fruit cell culture may be derived from any part of a plant including, but not limited to endosperm, aleurone layer, embryo (or its parts as scutellum and cotyledons), pericarp, stem, leaves, tubers, trichomes and roots.

According to some embodiments of the invention, although the amount of materials, including polyphenols, may vary in fruit, the use of a culturing protocol for preparing the fruit cell cultures ensures the reproducibility of the preparation and its contents. Thus, various batches of fruit cells, prepared from the same culture have a typical HPLC fingerprint. According to some embodiments, the concentrations of the various materials in each batch may change, though, as mentioned above, if prepared from the same culture, the HPLC fingerprint is consistent for all batches.

According to further embodiments, the composition is designed for a mucosal delivery.

According to some embodiments, the composition is tasteless. According to some embodiments, the composition is tasteful.

According to some embodiments, the composition is an oral composition. According to other embodiments, the composition is in a form of a mouthwash, a strip, a foam, a powder, a chewing gum, an oral spray, a lozenge, a capsule, a and toothpaste. According to yet another embodiment, the composition is in a form of a powder.

According to some embodiments, the fruit cell cultures do not include alcohol so as to avoid alcohol associated effects such as alcoholism, liver poisoning and heart failure.

Embodiments of the invention are directed to methods of treating, reducing, alleviating and/or preventing metabolic syndrome or metabolic malady or any condition or complication associated with metabolic syndrome or metabolic malady, such as, hypertension, diabetes, hyperlipidemia, impaired glucose tolerance, Hepatic steatosis, hyperglycemia, pre-diabetic state, New onset diabetes, Insulin resistance, Diabetes Mellitus, Impaired fasting glucose, hypertriglyceridemia, hypercholesterolemia, low HDL levels, fatty liver or obesity, comprising administering an alcohol free composition that comprises a cell line callus culture of fruit cells grown in vitro, and less than 1% alcohol.

According to some embodiments, the cell line callus culture of fruit cells is a cell line callus culture of grape berry cells. According to some embodiments, the cell line callus culture of grape berry cells is derived from one or more of grape-berry cross section, grape-berry skin, grape-berry flesh, grape seed, grape embryo of seeded or seedless cultivars or grape seed coat. According to further embodiments, the composition is a nutraceutical or pharmaceutical composition or a food additive.

In order to avoid problems associated with sugar intake, (e.g. obesity, diabetes, tooth caries), according to some embodiments, the fruit cultures contain less than 10% w/v sweetening sugar. As used herein, the phrase "a sweetening sugar" refers to a sugar which provides a sweet taste e.g. sucrose, glucose and fructose Embodiments of the invention are directed to methods of treating, reducing, alleviating and/or preventing metabolic syndrome or any condition or complication associated with metabolic syndrome or metabolic malady, such as, hypertension, diabetes, hyperlipidemia, impaired glucose tolerance, Hepatic steatosis, hyperglycemia, pre-diabetic state, New onset diabetes, Insulin resistance, Diabetes Mellitus, Impaired fasting glucose, hypertriglyceridemia, hypercholesterolemia, low HDL levels, fatty liver or obesity, comprising administering a low sugar composition that comprises a cell line callus culture of fruit cells grown in vitro, which comprise less than 10% sweetening sugar. According to some embodiments, the amount of the sweetening sugar is less than 5%. According to some embodiments, the amount of the sweetening sugar is less than 2%. According to some embodiments, the amount of the sweetening sugar is less than 1%. According to some embodiments, the amount of the sweetening sugar is between 0.5-1%.

According to some embodiments, the cell line callus culture of fruit cells is a cell line callus culture of grape berry cells. According to further embodiments, the composition is a nutraceutical or pharmaceutical composition or a food additive or functional foods and functional beverages. Typically, the amount of the powder that may be taken by a subject can range from at least 1 mg, 5 mg, 10, mg, 15 mg, 20 mg, 25 mg, 30 mg, 35 mg, 40 mg, 45 mg, 50 mg, 70 mg, 90 mg, 100 mg, 120 mg, 140 mg, 160 mg, 180 mg, 200 mg, 250 mg, 300 mg, 350 mg, 400 mg, 450 mg, 500 mg, 550 mg, 600 mg, 650 mg, 700 mg, 750 mg, 800 mg, 900 mg, 1000 mg, 1100 mg, 1500 mg, 1700 mg, 2000 mg and so forth to 50 gram per dose. In some embodiments the amount is about 5-10 mg, 10-20 mg, 20-30 mg, 30-40 mg, 40-50 mg, 50-60 mg, 60-70 mg, 70-80 mg, 90-100 mg, 100-200 mg, 200-300 mg, 300-400 mg, 400-500 mg, 500-600 mg, 600-700 mg, 700-800 mg, 800-900 mg, 900-1000 mg, 1-2 g, 2-3 g, 3-4 g, 4-5 g, 5-10 g or 10-50 g depending on the age and weight of the subject as well as the dosage regimen. In any case, the amount of a composition to be administered will be dependent on the subject being treated, the severity of the affliction, the manner of administration, the judgment of the physician, etc. The composition may be taken once to three times a day or if required more than three times a day. The composition may be taken chronically or for a certain period of time e.g. for at least one week, two weeks, one month, two months, three months, four months or more.

As can be seen in the Example 4, body weight, systolic BP, plasma triglyceride, insulin and adiponectin levels were measured in rats fed with high fructose diet at baseline and after three and five weeks of diet. High fructose diet induced a significant rise in blood pressure, plasma triglycerides, insulin and adiponectin levels. The effect of red grape culture (RGC) was tested on the fed rats. The addition of fruit cell cultures attenuated blood pressure rise induced by high fructose diet (FIG. 5) as well as the rise in plasma triglycerides and insulin levels induced by high fructose diet. Further, the effect of fruit cell cultures on blood pressure was observed already after two weeks of treatment and at the dose of red grape culture which contains only 4 mg of resveratrol. This may be attributed to the unique combination of natural resveratrol and other grape polyphenols in the RGC. In some embodiments, the effective dose of resveratrol on systolic blood pressure, insulin resistence and triglycerides level is between 4 (200 mg/Kg/day of RGC powder) to 16 (800 mg/Kg/day of RGC powder) mg. In some embodiments, the effective dose of resveratrol on systolic blood pressure, insulin resistence and triglycerides level is between 0.5 (50 mg/Kg/day of RGC powder) to 40 (2400 mg/Kg/day of RGC powder) mg.

It is noted that the high fructose diet was used to induce the metabolic syndrome in SD rats. This induction is supported by the increase in systolic blood pressure, triglycerides and insulin levels in rats fed with a high fructose diet. In this model system, supplementation of RGC not only lowered BP but also improved the other symptoms of metabolic syndrome.

According to another embodiment of the invention, the cell culture may be derived from any part of a plant including, but not limited to endosperm, aleurone layer, embryo (or its parts as scutellum and cotyledons), pericarp, stem, leaves, tubers, trichomes and roots.

Formulations suitable for oral administration may be prepared as discrete units such as powder, pills, troches, lozenges, capsules, cachets or tablets each containing a predetermined amount of the fruit cell culture.

The phrase "therapeutically effective amount" means an amount of a compound of the present invention that (i) treats the particular disease, condition, or disorder, (ii) attenuates, ameliorates, or eliminates one or more symptoms of the particular disease, condition, or disorder, or (iii) delays the onset of one or more symptoms of the particular disease, condition, or disorder described herein. In certain embodiments a therapeutically effective amount may achieve one or more of lowering blood glucose level, increasing insulin secretion, decreasing glucagon secretion, decreasing insulin resistance and increasing insulin sensitivity.

Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom.

Aqueous or oil suspensions, dispersible powders or granules, emulsions, hard or soft capsules, e.g. gelatin capsules, syrups or elixirs may be prepared for oral use Faster absorption may be affected by increasing flavor levels as well as the addition of other flavor components, such as menthol and menthol derivatives, limonene, carvone, isomenthol, eucalyptol, menthone, pynene, camphor and camphor derivatives, as well as monoterpene natural products, monoterpene derivatives, and sesquaterpenes, including caryophyllene and copaene.

The formulations may include other agents that enhance the delivery of the active agents to the bloodstream. Examples of such agents include, but are not limited to 23-lauryl ether, Aprotinin, Azone, Benzalkonium chloride, Cetylpyridinium chloride, Cetyltrimethylammonium bromide, Cyclodextrin, Dextran sulfate, Lauric acid, Lauric acid/Propylene glycol, Lysophosphatidylcholine, Menthol, Methoxysalicylate, Methyloleate, Oleic acid, Phosphatidylcholine, Polyoxyethylene, Polysorbate 80, Sodium EDTA, Sodium glycocholate, Sodium glycodeoxycholate, Sodium lauryl sulfate, Sodium salicylate, Sodium taurocholate, Sodium taurodeoxycholate, Sulfoxides and various alkyl glycosides Other modifications may also affect the release rate of the active agents. Texture modifiers to soften base may give faster release where hard bases may give slower release. Addition of alkaline materials, such as sodium bicarbonate or sodium hydroxide, may make the saliva slightly alkaline, which may increase buccal/lingual absorption of the medicament into the bloodstream Release of the active agents of the present invention may also be affected by the shape and size of the formulation. For example, flat stick pieces of gum with large surface area may release actives faster into saliva from gum when chewed, whereas round or cube pieces may release medicaments and actives more slowly.

Tableting of chewing gum is disclosed in U.K. Patent Publication No. 1,489,832; U.S. Pat. No. 4,753,805; EP Patent Publication No. 0 221 850; and Italy Patent Publication No. 1,273,487. These patents disclose active agents added to chewing gum which is then tableted.

Coloring agents may also be added to the formulations. According to some embodiments the coloring agents include food quality dyes. According to some embodiments, film formers may be added to the formulations. Film formers that may be added to the formulation include methyl cellulose, gelatins, hydroxypropyl cellulose, ethyl cellulose, hydroxyethyl cellulose, carboxymethyl cellulose and combinations thereof. According to another embodiment, fruit cell cultures of the present invention are provided in a non-coloring concentration.

For administration by nasal inhalation, the active ingredients may be conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

According to some embodiments, the fruit cell cultures and preparations derived therefrom may also be provided as food additives and ingested orally.

According to some embodiments, the food additive and food ingredient composition may be added to a variety of food products. According to further embodiments, the fruit cell cultures are added to foods that are retained in the mouth prior to swallowing so as to enhance delivery into the bloodstream. Examples of such foods include chocolates, sweets and ice-creams, dairies, bars, bread, cereals, yogurt as well as beverages.

As used herein, the phrase "food product" describes a material consisting essentially of protein, carbohydrate and/or fat, which is used in the body of an organism to sustain growth, repair and vital processes and to furnish energy. Food products may also contain supplementary substances such as minerals, vitamins and condiments. See Merriani-Webster's Collegiate Dictionary, 10th Edition, 1993. The phrase "food product" as used herein further includes a beverage adapted for human or animal consumption.

A food product containing the formulation according to some embodiments may also include additional additives such as, for example, antioxidants, sweeteners, flavorings, colors, preservatives, nutritive additives such as vitamins and minerals, amino acids (i.e. essential amino acids), emulsifiers, pH control agents such as acidulants, hydrocolloids, antifoams and release agents, flour improving or strengthening agents, raising or leavening agents, gases and chelating agents, the utility and effects of which are well-known in the art.

Toxicity and therapeutic efficacy of the active ingredients may be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

In some embodiments of the invention, there is provided a composition in a form of a powder for use for treating, alleviating or preventing metabolic syndrome comprising a cell line callus culture of grape berry cells grown in vitro in a large scale up process, whereby the cell line callus culture of grape berry cells is derived from one or more of grape-berry cross section, grape-berry skin, grape-berry flesh, grape seed, grape embryo of seeded or seedless cultivars or grape seed coat; wherein the cell line callus culture of grape berry cells includes resveratrol in an amount of at least 1000 mg/kg powder. In some embodiments of the invention, at least 90% of the resveratrol in the grape cells manufactured in accordance with the embodiments of the large scale process described herein is trans-glucoside resveratrol.

According to some embodiments, the relative amounts of the various polyphenols in the prepared fruit cells, differ from the relative amounts thereof in the agricultural grape fruit. This can be clearly seen in Example 3, Table 9 in which the total resveratrol in dried grape cell culture produced in large scale in accordance with the embodiments of the invention was compared to the amount of the resveratrol in grapes. According to some embodiments, the amount of certain polyphenols is amplified in the prepared fruit cells, in comparison to their amount in the agricultural grape fruit. According to some embodiments, the amount of the resveratrol is amplified in the fruit cells. According to some embodiments, the amount of resveratrol in the fruit cells, which may be grape cells, is between 1000-50000 mg/kg, after the fruit cells, which may be grape cells are dried to a powder. According to some embodiments of the invention, the amount is more than 1000 mg/kg after the fruit cells are dried to a powder. According to some embodiments of the invention, the amount is more than 3000 mg/kg after the fruit cells are dried to a powder. According to some embodiments of the invention, the amount is more than 5000 mg/kg after the fruit cells are dried to a powder. According to some embodiments of the invention, the amount is more than 10000 mg/kg after the fruit cells are dried to a powder. According to some embodiments of the invention, the amount is more than 20000 mg/kg after the fruit cells are dried to a powder. According to some embodiments of the invention, the amount is more than 30000 mg/kg after the fruit cells are dried to a powder. According to some embodiments of the invention, the amount is more than 40000 mg/kg after the fruit cells are dried to a powder. According to some embodiments of the invention, the amount is more than 50000 mg/kg after the fruit cells are dried to a powder. According to some embodiments of the invention, the amount is more than 60000 mg/kg after the fruit cells are dried to a powder. According to some embodiments of the invention, the amount is more than 70000 mg/kg after the fruit cells are dried to a powder.

According to some embodiments, the relative amounts of various ingredients in the prepared fruit cells, differ from the relative amounts thereof in the agricultural grape fruit. According to some embodiments, the relative amount of sugar in the fruit cells is reduced in comparison to the relative amount of the sugar in the agricultural grape fruit.

According to one embodiment, the dried fruit cells contains up to 10% w/v sweetening sugar. According to some embodiments of the invention, the dried fruit cells contains up to 15% w/v sweetening sugar. According to one embodiment, the dried fruit cells contain between 10-15% w/v sweetening sugar. According to one embodiment, the dried fruit cells contain between 15-20% w/v sweetening sugar. According to some embodiments, the fruit cells prepared according to the large scale method of the invention contain less than 10% w/v sweetening sugar. According to some embodiments, the fruit cells contain less than 5% w/v sweetening sugar. According to some embodiments, the fruit cells contain less than 3% w/v sweetening sugar. According to some embodiments, the fruit cells contain less than 2% w/v sweetening sugar. According to some embodiments, the fruit cells contain less than 1% w/v sweetening sugar. According to some embodiments, the fruit cells contain about 1% w/v sweetening sugar. As used herein, the phrase "a sweetening sugar" refers to a sugar which provides a sweet taste e.g. sucrose, glucose and fructose.

According to one embodiment, the dried fruit cells contain less than 20% w/v sweetening sugar. According to one embodiment, the dried fruit cells contain less than 30% w/v sweetening sugar.

According to some embodiments, the fruit cells are dried, thus concentrating the materials found therein, including the sugar. According to some embodiments, the materials are concentrated by a factor of 5. According to some embodiments, the materials are concentrated by a factor of 10. According to some embodiments, the materials are concentrated by a factor of 15. According to some embodiments, the materials are concentrated by a factor of 20. According to some embodiments, the materials are concentrated by a factor of 25. According to some embodiments, the materials are concentrated by a factor of 30.

According to some embodiments, the fruit cells prepared according to the large scale method of the invention are tasteless According to other embodiments, the fruit cells prepared according to the large scale method of the invention are tasteful. Embodiments of the invention are directed to a process for the large scale in vitro production of fruit cells. In Some embodiments of the invention, the process does not include the extraction of the fruit cells. Surprisingly, the produced fruit cells manufactured in accordance with the large scale process described herein were shown to include high amount of polyphenols.

In one embodiment of the invention, there is provided a large scale process for the in vitro production of a cell line callus culture of grape berry cells grown comprising:
growing grape cells in a flask;
inoculating the grape cells from the flask into a first bioreactor; and harvesting the produced grape cells.

In some embodiments of the invention, there is provided a large scale process for the in vitro production of a cell line callus culture of grape berry cells grown comprising:
growing grape cells in a flask;
inoculating the grape cells from the flask into a first bioreactor; inoculating the grape cells from the first bioreactor into another bioreactor, wherein the another bioreactor is a last bioreactor or an intermediate bioreactor and there may be provided some more steps with one or more intermediate bioreactor and wherein at least one of the first and the another bioreactor is disposable; and harvesting the grape cells from the last bioreactor;

wherein the grape cells harvested from the last bioreactor are dried.

By a "disposable bioreactor" it is meant a bioreactor with a disposable bag, which can be for a single use bag instead of a culture vessel. The disposable bag is typically made of three layers or more plastic foil. In some embodiments of the invention, one layer is made from polyethylene, polyethylene terephthalate or LDPE to provide mechanical stability. A second layer is made using nylon, PVA or PVC that acts as a gas barrier. Finally, a contact layer is made from PVA or PP or another layer of polyethylene, polyethylene terephthalate or LDPE. For medical applications the single-use materials that contact the product must be certified by the European Medicines Agency or similar authorities responsible for other regions.

According to some embodiments of the invention, the disposable bioreactor is made from one or more layers of polyethylene. In some embodiments of the invention, the disposable bioreactor is made from an inner and outer layer of polyethylene and a middle nylon layer.

In general there are two different approaches for constructing single-use bioreactors, differing in the means used to agitate the culture medium.

Some single-use bioreactors use stirrers like conventional bioreactors, but with stirrers that are integrated into the plastic bag. The closed bag and the stirrer are pre-sterilized. In use the bag is mounted in the bioreactor and the stirrer is connected to a driver mechanically or magnetically.

Other single-use bioreactors are agitated by a rocking motion. Other single-use bioreactors are airlift bioreactor in which the reaction medium is agitated and aerated by introduction of air. This type of bioreactor does not need any mechanical agitators inside the single-use bag.

According to some embodiments, the large scale process for preparing fruit cells is comprised of a number of subsequent steps. According to some embodiments of the invention, the amount of fruit cells prepared in each step is larger than that prepared in the previous step. Further, the fruit cells prepared in each step are inoculated or harvested to be used as a starter for the next step of the large scale process. In the last step of the large scale process, the fruit cells are typically grown until they reach the plateau in their growth profile.

The advantages of using the large scale process of the invention are clear and demonstrated in the Examples section. As can be seen in Example 2, experiment 2, the Red Grape Cells (RGC) biomass with enriched Gamborg B5 medium was much higher in comparison to the biomass obtained in the presence of non-enriched Gamborg B5 medium. Further, the use of Gamborg B5 medium containing different concentrations of magnesium, nitrates and phosphates ($KNO_3$, $MgSO_4$, $MgNO_3$, $NaH_2PO_4$) salts resulted in high resveratrol level in the produced cells, even in the large scale bioreactor.

Table 4 and Example 2, experiment 3 shows that the level of total polyphenols as well as of resveratrol in enriched medium, in the grape cells grown in the large scale disposable bioreactors was higher than the level obtained in the grape cells grown in Erlenmeyer flask, namely 910 mg/l and 203 mg/l, respectively. In contrast to observations made by others, this is the first time to demonstrate successful growth of fruit plant cells in large scale disposable bioreactor of 1000-5000 liter with high level of resveratrol and polyphenols production.

Table 7 and Example 2, experiment 7 show the effect of two mediums, IM1 medium and Gamborg B5 enriched with magnesium, phosphate and nitrates salts on the amount of resveratrol produced by the cells. The effect was assessed in 20 L bioreactors made of a sterilized, disposable, transparent plastic container and further compared to data published in A. Decendit (1996) Biotechnology Letters, where cells were grown in IM1 medium in a 20 L glass container. The results demonstrate that Red Grape Cells grown in IM1 medium in a disposable bioreactor produced 93 mg/l of resveratrol (Table 7) which is approximately three fold higher than the level produced in stirred glass bioreactor using the same medium (Decendit). Moreover, significant high level of resveratrol, 387 mg/l, was produced when these cells were grown in enriched Gamborg B5 in disposable bioreactor. Thus, this experiment shows the advantages of using a disposable bioreactor or bioreactors and the Gamborg B5 medium containing different concentrations of magnesium, nitrates and phosphates ($KNO_3$, $MgSO_4$, $MgNO_3$, $NaH_2PO_4$) salts as well as the advantages of using the combination of a disposable bioreactor or bioreactors and an enriched Gamborg B5 medium.

According to some embodiments, the fruit cells are grown in bioreactors. According to some embodiments, the bioreactors are designed so as to allow adequate mixing and mass transfer, while minimizing the intensity of shear stress and hydrodynamic pressure. According to some embodiments of the invention, at least one of the bioreactors is a disposable bioreactor. This can be the first bioreactor or the intermediate bioreactor or the last bioreactor or any combination thereof. According to some embodiments of the invention, the disposable bioreactor is the last bioreactor after which the cells are harvested and dried so as to form a powder.

According to an exemplary embodiment of the invention, the first step includes the preparation of a fruit cell culture in a flask, such as an Erlenmeyer or a bioreactor. According to some embodiments, the first step involves the preparation of up to 1.0 L of a fruit cell culture. According to further embodiments, first step involves the preparation of up to 1.5 L of a fruit cell culture. According to further embodiments, first step involves the preparation of up to 2.0 L of a fruit cell culture.

According to some embodiments, the first step is conducted using a glass, metal or plastic flask. According to some embodiments, the flask is disposable. According to further embodiments, the flask may be reused any number of times. According to some embodiments, the flask is sterilized by any appropriate means between uses.

According to some embodiments, the first step includes the use of any appropriate medium for growing the fruit cells. According to some embodiments, the medium used for growing the fruit cells includes cell growth medium, salts, vitamins, sugars, hormones or any combination thereof. According to some embodiments, the cell growth medium is B5 Gamborg (Gamborg et al., Exp. Cell Res. 50:151, 1968), or any modification thereof. According to some embodiments, the Gamborg B5 comprises salts such as magnesium, phosphate, nitrate or any combination thereof. According to some embodiments of the invention, the Gamborg B5 medium includes $KNO_3$, $MgSO_4$, $NaH_2PO_4$, or any combination thereof. According to some embodiments, the medium includes Gamborg B5 vitamins or any combination thereof. According to further embodiments, the medium includes sugars such as sucrose, Gamborg B5 or any combination thereof.

In an embodiment of the invention, the concentration of the $KNO_3$ added to the Gamborg B5 is between 25 mM to 45 mM.

In an embodiment of the invention, the concentration of the $MgSO_4$ added to the B5 Gamborg is between 1 mM to 15 mM.

In an embodiment of the invention, the concentration of the $MgNO_3$ added to the B5 Gamborg is between 5 mM to 35 mM.

In an embodiment of the invention, the concentration of the $KNO_3$ added to the Gamborg B5 is between 15 mM to 60 mM.

In an embodiment of the invention, the concentration of the $MgSO_4$ added to the B5 Gamborg is between 0.5 mM to 25 mM.

In an embodiment of the invention, the concentration of the $MgNO_3$ added to the B5 Gamborg is between 1 mM to 50 mM.

In an embodiment of the invention, the concentration of the $KNO_3$ added to the Gamborg B5 is between 30 mM to 40 mM.

In an embodiment of the invention, the concentration of the $MgSO_4$ added to the B5 Gamborg is between 5 mM to 10 mM.

In an embodiment of the invention, the concentration of the $MgNO_3$ added to the B5 Gamborg is between 20 mM to 30 mM.

In an embodiment of the invention, myo-inositol is added to the Gamborg B5

In an embodiment of the invention, $H_3BO_3$ added to the Gamborg B5

In an embodiment of the invention, $MnSO_4$ added to the Gamborg B5.

In an embodiment of the invention, $NaH_2PO_4$ is added to the Gamborg B5.

In an embodiment of the invention, Biotin is added to the Gamborg B5

In an embodiment of the invention, mM D-Pantothenate calcium is added to the Gamborg B5.

In an embodiment of the invention, about 0.5 mM myo-inositol is added to the Gamborg B5

In an embodiment of the invention, about 0.05 mM $H_3BO_3$ added to the Gamborg B5

In an embodiment of the invention, about 0.04 mM $MnSO_4$ added to the Gamborg B5.

In an embodiment of the invention, about 1 mM $NaH_2PO_4$ is added to the Gamborg B5.

In an embodiment of the invention, about 0.004 mM Biotin is added to the Gamborg B5

In an embodiment of the invention, about 0.2 mM D-Pantothenate calcium is added to the Gamborg B5.

In an embodiment of the invention, about 0.1, 0.2, 0.3, 0.4, 0.5, 0.6, 0.7, 0.8, 0.9, 1.0, 2, 3, 4, 5, 6, 7, 8, 9, 10 mM myo-inositol is added to the Gamborg B5.

In an embodiment of the invention, about 0.01, 0.02, 0.03, 0.04, 0.05, 0.06, 0.07, 0.08, 0.09, 0.1 mM $H_3BO_3$ is added to the Gamborg B5.

In an embodiment of the invention, about 0.01, 0.02, 0.03, 0.04, 0.05, 0.06, 0.07, 0.08, 0.09, 0.1 mM $MnSO_4$ is added to the Gamborg B5.

In an embodiment of the invention, 0.1, 0.2, 0.3, 0.4, 0.5, 0.6, 0.7, 0.8, 0.9, 1.0, 2, 3, 4, 5, 6, 7, 8, 9, 10 mM $NaH_2PO_4$ is added to the Gamborg B5.

In an embodiment of the invention, about 0.001, 0.002, 0.003, 0.004, 0.005, 0.006, 0.007, 0.008, 0.009, 0.01 mM Biotin is added to the Gamborg B5

In an embodiment of the invention, about 0.1, 0.2, 0.3, 0.4, 0.5, 0.6, 0.7, 0.8, 0.9, 1.0, 2, 3, 4 mM D-Pantothenate calcium is added to the Gamborg B5.

In an embodiment of the invention, the concentration of the sucrose added to the Gamborg B5 is between 2 to 4%. In another embodiment, the concentration is about 3%.

According to further embodiments, casein may be included in the cell growth medium. According to further embodiments growth hormones may be included in the cell growth medium. According to further embodiments, the growth medium includes hormones. According to some embodiments the fruit cells are grown without the addition of hormones.

Examples of plant culture media that may be used according to some embodiments in one stage or more of the process, include, but are not limited to: Anderson (Anderson, In Vitro 14:334, 1978; Anderson, Act. Hort., 112:13, 1980), Chee and Pool (Sci. Hort. 32:85, 1987), CLC/*Ipomoea* (CP) (Chee et al., J. Am. Soc. Hort. Sci. 117:663, 1992), Chu (N.sub.6) (Chu et al., Scientia Sinic. 18:659, 1975; Chu, Proc. Symp. Plant Tiss. Cult., Peking 43, 1978), DCR (Gupta and Durzan, Plant Cell Rep. 4:177, 1985), DKW/*Juglans* (Driver and Kuniyuki, HortScience 19:507, 1984; McGranahan et al., in: Bonga and Durzan, eds., Cell and Tissue Culture in Forestry, Martinus Nijhoff, Dordrecht, 1987), De Greef and Jacobs (De Greef and Jacobs, Plant Sci. Lett. 17:55, 1979), Eriksson (ER) (Eriksson, Physiol. Plant. 18:976, 1965), Gresshoff and Doy (DBM2) (Gresshoff and Doy, Z Pflanzenphysiol. 73:132, 1974), Heller's (Heller, Ann. Sci. Nat. Bot. Biol. Veg. 11th Ser. 14:1, 1953), Hoagland's (Hoagland and Amon, Circular 347, Calif. Agr. Exp. Stat., Berkeley, 1950), Kao and Michayluk (Kao and Michayluk, Planta 126:105, 1975), Linsmaier and Skoog (Linsmaier and Skoog, Physiol. Plant. 18:100, 1965), Litvay's (LM) (Litvay et al., Plant Cell Rep. 4:325, 1985), Nitsch and Nitsch (Nitsch and Nitsch, Science 163:85, 1969), Quoirin and Lepoivre (Quoirin et al., C. R. Res. Sta. Cult. Fruit Mar., Gembloux 93, 1977), Schenk and Hildebrandt (Schenk and Hildebrandt, Can. J. Bot. 50:199, 1972), White's (White, The Cultivation of Animal and Plant Cells, Ronald Press, N Y, 1963), etc.

According to some other exemplary embodiments, the fruit cells and the medium are continuously mixed during the first step. According to further embodiments, the fruit cells and the medium are mixed occasionally during the first step. According to some embodiments, the temperature during the first step is between 20° C. and 30° C. According to some embodiments, the temperature during the first step is between 22° C. and 28° C. According to some embodiments, the fruit cells are grown in the first step for more than 5 days. According to some embodiments, the fruit cells are grown in the first step for more than 7 days. According to some embodiments, the fruit cells are grown in the first step for more than 5 days and less than 2 weeks. According to some embodiments, the fruit cells are grown in the first step for more than 5 days and less than 12 days.

According to some exemplary embodiments, the bioreactor used in the process of invention includes an inlet through which the fruit cells from the first step, the medium and any additional materials are placed into the bioreactor. According to further embodiments, the bioreactor used in the process of the invention includes an outlet for removing any materials desired. According to some embodiments, the outlet includes a gas outlet, designed to relieve the bioreactor of excess gases. According to some embodiments, the gas outlet is operated manually. According to other embodiments, the gas outlet is operated automatically, wherein gases are let out of the flask once the atmosphere in the flask reaches a pre-defined pressure. According to some embodiments, the predefined pressure up to 8 PSI.

Once the first step of the fruit cell growth is concluded, according to some exemplary embodiments, the fruit cells are inoculated into a small scale bioreactor, which is termed here also the first bioreactor. For the second step of the large scale process. According to some embodiments, the small scale bioreactor is a 4 L reactor. According to further embodiments, the small scale bioreactor is a 3-5 L reactor. According to further embodiments, the small scale bioreactor is a 3-10 L reactor. According to further embodiments, the small scale bioreactor is a 4-8 L reactor.

The small scale bioreactor may be prepared from any appropriate material, such as glass, metal, plastic and/or any type of polymer. According to some embodiments, the small scale bioreactor is disposable. If the small scale bioreactor is not disposable, according to some embodiments, it is cleaned and sterilized between uses by any appropriate means.

As described above, the production of secondary metabolites, including polyphenols, such as resveratrol, is known to be significantly reduced when larger quantities of fruit cells are grown in bioreactors, in comparison to the amount of the same metabolites in small scale productions, using, e.g., glass flasks, such as Erlenmeyers. However, the large scale process detailed herein provides fruit cells in which the amount of the secondary metabolites is not reduced when grown in bioreactors. Further, the production of certain secondary metabolites may even be amplified.

Thus, according to embodiments of the invention, the relative amounts of the secondary metabolites in fruit cells grown in the small scale bioreactor are not significantly reduced in comparison to their relative amounts in the first step of the process. According to some embodiments, the components described above for use in the growth medium in the first step may be used also in the second step of the process. According to some embodiments, the growth medium used in the small scale bioreactor is the same as used in the first step of the large scale process. According to some embodiments, the relative amounts of the different components found in the growth medium in the second step, is the same as in the first step. According to other embodiments, the relative amounts of the different components found in the growth medium in the second step, differ from the relative amounts used in the first step. According to some embodiments, additional materials are added to the growth medium in the second step of the process.

According to some embodiments, the small scale bioreactor includes an inlet through which the fruit cells from the first step, air, the medium and any additional materials are placed into the bioreactor. According to further embodiments, the small scale bioreactor includes an outlet for removing any materials desired. According to some embodiments, the outlet includes a gas outlet, designed to relieve the bioreactor of excess gases. According to some embodiments, the gas outlet is operated manually. According to other embodiments, the gas outlet is operated automatically, wherein gases are let out of the bioreactor once the atmosphere in the bioreactor reaches a pre-defined pressure. According to some embodiments, the predefined pressure is 8 PSI.

According to some embodiments, the fruit cells and the medium are continuously mixed during the second step. According to further embodiments, the fruit cells and the medium are mixed occasionally during the second step. According to some embodiments, the temperature during the second step is between 20 to 30 Celsius degrees. According to some embodiments, the fruit cells are grown in the second step for more than a week and less than two weeks. In some embodiments of the invention, the fruit cells are grown between 9-16 days before being inoculated into the next bioreactor.

For the third step of the large scale process, the harvested fruit cells are placed into a large scale bioreactor. According to some embodiments, the large scale bioreactor is a 30-50 L reactor. According to further embodiments, the large scale bioreactor is a 40-60 L reactor. According to further embodiments, the large scale bioreactor is a 30-70 L reactor. According to further embodiments, the large scale bioreactor is a 20-100 L reactor.

The large scale bioreactor may be prepared from any appropriate material, such as glass, metal, plastic and/or any type of polymer. According to some embodiments, the large bioreactor is disposable. If the large scale bioreactor is not disposable, according to some embodiments, it is cleaned and sterilized between uses by any appropriate means.

Similarly to the small scale bioreactor, according to embodiments of the invention, the relative amounts of the secondary metabolites in fruit cells grown in the large scale bioreactor are not significantly reduced in comparison to their relative amounts in any of the previous steps of the process. According to some embodiments, the components described above for use in the growth medium in any of the previous steps may be used also in the third step of the process. According to some embodiments, the growth medium used in the large scale bioreactor is the same as used in any of the previous steps of the large scale process. According to some embodiments, the relative amounts of the different components found in the growth medium in the third step, is the same as in any of the previous steps of the process. According to other embodiments, the relative amounts of the different components found in the growth medium in the third step, differs from the relative amounts used in any of the previous steps of the process. According to some embodiments, additional materials are added to the growth medium in the third step of the process.

According to some embodiments, the large scale bioreactor includes an inlet through which the fruit cells from the second step, the medium, air and any additional materials are placed into the bioreactor. According to further embodiments, the large scale bioreactor includes an outlet for removing any materials desired. According to some embodiments, the outlet includes a gas outlet, designed to relieve the bioreactor of excess gases. According to some embodiments, the gas outlet is operated manually. According to other embodiments, the gas outlet is operated automatically, wherein gases are let out of the bioreactor once the atmosphere in the bioreactor reaches a pre-defined pressure. According to some embodiments, the predefined pressure is up to 8 PSI.

According to some exemplary embodiments, the fruit cells and the medium are continuously mixed during the third step. According to further embodiments, the fruit cells and the medium are mixed occasionally during the third step. According to some embodiments, the temperature during the third step is between 20 and 30. According to some embodiments, the fruit cells are grown in the third step for about two to three weeks. According to some embodiments, the fruit cells are grown in the third step for about three to five weeks. According to some embodiments, the fruit cells are grown in the third step for about 12 to 30 days.

Once the third step of the fruit cell growth is concluded, the fruit cells are inculcated from the medium scale bioreactor typically by any appropriate means. For the fourth exemplary step of the large scale process, the harvested fruit cells are placed into a larger scale bioreactor. According to some embodiments, the larger scale bioreactor is a 1000 L reactor. According to further embodiments, the larger scale bioreactor is a 200-500 L reactor. According to further embodiments, the large scale bioreactor is a 500-1000 L reactor. According to further embodiments, the large scale bioreactor is a 1000-1500 L reactor. According to further embodiments, the large scale bioreactor is a 500-1100 L reactor.

The larger scale bioreactor may be prepared from any appropriate material, such as glass, metal, plastic and/or any type of polymer. According to some embodiments, the large scale bioreactor is disposable. If the large scale bioreactor is not disposable, according to some embodiments, it is cleaned and sterilized between uses by any appropriate means.

Similarly to the small scale bioreactors, according to embodiments of the invention, the relative amounts of the secondary metabolites in fruit cells grown in the larger scale bioreactor are not significantly reduced in comparison to their relative amounts in the previous steps of the process. According to some embodiments, the components described above for use in the growth medium in any of the previous steps may be used also in the fourth step of the process. According to some embodiments, the growth medium used in the larger scale bioreactor is the same as used in any of the previous steps. According to some embodiments, the relative amounts of the different components found in the growth medium in the fourth step, is the same as in any of the previous steps. According to other embodiments, the relative amounts of the different components found in the growth medium in the fourth step, differs from the relative amounts used in any of the previous steps. According to some embodiments, additional materials are added to the growth medium in the fourth step of the process.

According to some embodiments, the larger scale bioreactor includes an inlet through which the fruit cells from the third or second step, the medium and any additional materials are placed into the bioreactor. According to further embodiments, the larger scale bioreactor includes an outlet for removing any materials desired. According to some embodiments, the outlet includes a gas outlet, designed to relieve the bioreactor of excess gases. According to some embodiments, the gas outlet is operated manually. According to other embodiments, the gas outlet is operated automatically, wherein gases are let out of the bioreactor once the atmosphere in the bioreactor reaches a pre-defined pressure.

According to some embodiments, the fruit cells and the medium are continuously mixed during the fourth step. According to further embodiments, the fruit cells and the medium are mixed occasionally during the fourth step. According to some embodiments, the temperature during the fourth step is between 20 to 30. According to some embodiments, the fruit cells are grown in the third or fourth step until they reached a cell biomass of 10% to 70%.

According to some embodiments, the large scale process is terminated after the fruit cells are grown in the larger scale bioreactor. According to such embodiments, the fruit cells are grown in the larger scale bioreactor until they reach a cell biomass of 10% to 70%. Once the cell biomass of 10% to 70%. is reached, the fruit cells are harvested from the large scale bioreactor by any appropriate means and are further processed. According to some embodiments, the fruit cells are further processed by drying, lyophilization, Freeze-Drying and Spray Drying. According to some embodiments, the processing of the fruit cells does not include the extraction of active ingredients therefrom.

According to some embodiments, the large scale process may include one step of inoculating the cells from a flask into a bioreactor which can be in any size and harvesting the cells. According to other embodiments, the fruit cells may be inculcated in a series of bioreactors wherein each of the bioreactors is typically larger than the previous bioreactor used. Any number of additional steps is performed according to the large scale process. The additional steps include possible intermediate steps in which the cells are harvested or inoculated and placed in a larger bioreactor and grown there until being harvested or inoculated and transferred to a larger bioreactor. According to further embodiments, the process includes additional steps for growing the fruit cells harvested from the large scale bioreactor.

Various aspects of the invention are described in greater detail in the following Examples, which represent embodiments of this invention, and are by no means to be interpreted as limiting the scope of this invention.

EXAMPLES

Example 1

Manufacturing-Industrial Level Scaling Up
1. Material and Methods

The production process encompasses propagation of grape cells in a progressively process having five stages. Starting from propagation of grape cells in an Erlenmeyer shake flasks for further propagation in a small and large scale disposable bioreactor. The critical key factor is maintaining a high level of the secondary metabolite, resveratrol in the cells during the propagation in different bioreactors scale. At the end of the last large scale stage of propagation, at the required biomass, the cells are harvested and dried to produce a fine pink-purple powder yielding a biomass of dried cells (RGC) which are used for different medicinal applications.

Grape Cell Line Formation

Calli from grape cross sections: Young grape bunches, 4 to 8 cm long, were harvested from field grown grape plants 20-50 days post anthesis and were thoroughly rinsed in running tap water. Green immature berries of the seedless grape *Vitis vinifera* cv. "AVNIR 825" (a cross between Agraman and Gamay red) were sterilized for 10 minutes in a solution containing 1.3% w/v sodium hypochlorite and (0.1% v/v) Tween 20, as a wetting agent. Explants were dissected, using a scalpel, into 2 to 3 mm long traversal sections under half-strength MS (Murashige and Skoog, 1962, Physiol Plant 15:473-497) liquid basal medium supplemented with filter-sterilized 1.7 mM ascorbic acid and 0.8 mM citric acid, 100 mg/l DTT (dithiothreitol) and 50 mg/l acetyl cysteine. The following antioxidants were added to the cutting medium: PVP (0.5 and 1 g/l), L-cysteine (150 mg/)l, gallic acid (1.5 mg/l), DTT (70 mg/l), biopterin (15 mg/l), ascorbic acid (150 mg/l) and citric acid (150 mg/l) in order to inhibit cell necrogenesis and to enable the recovery of green, health berry disks.

Berry disks were placed in 100×15 mm culture plates containing 25 ml of autoclaved Murashige and Skoog, MS medium, solidified with 0.25% Gelrite. The pH was adjusted to pH 5.9 prior to autoclaving at 102 kpa for 15 minutes.

Thirty plates each containing 25 berry disks, were sealed with Parafilm and incubated in the dark at 26° C. for three days. Cultures were incubated at 25° C. under a 16-h photoperiod of 15-30 μmolm$^{-2}$ s$^{-1}$ irradiance provided by cool-white fluorescent tubes. MS salt and vitamins medium was also supplemented with 250 mg/l casein hydrolisate, 2% sucrose and 100 mg/l inositol. For callus induction it was also supplemented with 0.2 mg/l Kinetin and 0.1 mg/l NAA (α-naphthaleneacetic acid) media designated as RD1.

3-4 weeks following culture initiation, a mixture of green and red callus was visible along the berry disks. The callus was composed of friable, elongated cells, some of which exhibited a dark pigmentation of anthocyanins. Callus sector enriched in anthocyanins were selected and individually subcultured for propagation. Green callus sectors were cultured separately.

Calli from grape skin cells: Young grape bunches, 4 to 8 cm long, were harvested 20-50 days post anthesis from field grown grape plants and were thoroughly rinsed in running tap water. Green immature berries of the seedless grape *Vitis vinifera* cv. "AVNIR 825" (a cross between Agraman and Gamay red) were sterilized for 10 minutes in a solution containing 1.3% w/v sodium hypochlorite and (0.1% v/v) Tween 20, as a wetting agent. Berry skins were isolated by producing a cut of 3-8 mm in the berry skin and peeling off only the skins using a sterile forceps. Skin isolation was performed under half-strength MS (Murashige and Skoog, 1962) liquid basal medium supplemented with filter-sterilized 1.7 mM ascorbic acid and 0.8 mM citric acid, 100 mg/l DTT (dithiothreitol) and 50 mg/l acetyl cysteine.

Berry skins were placed in RD-1 culture media. Following about 10-14 days, cell clumps started to develop on the cut surface of the skin pills. Cell, enriched in anthocyanins, were selected and further subcultured into fresh media for further propagation.

Calli from grape seed coats: Young grape bunches, 4 to 8 cm long, were harvested 20-50 days post anthesis from field grown grape plants and were thoroughly rinsed in running tap water. Green immature berries of the seedless grape *Vitis vinifera* cv. "AVNIR 825" were sterilized for 10 minutes in a solution containing 1.3% w/v sodium hypochlorite and (0.1% v/v) Tween 20, as a wetting agent. Berries were cut open to reveal the young green developing seeds. Immature seed coats were dissected and placed on culture medium. Isolation was performed under half-strength MS (Murashige and Skoog, 1962) liquid basal medium supplemented with filter-sterilized 1.7 mM ascorbic acid and 0.8 mM citric acid, 100 mg/l DTT (dithiothreitol) and 50 mg/l acetyl cysteine.

The seed coat sections were placed in RD-1 culture media. After about 12-20 days, seed coats turned brown and a callus started to appear on top of the seed coat explants. Cell, enriched in red-brown pigmentation, were selected and further subcultured into fresh media for further propagation.

Establishment of liquid cultures: Liquid cultures were established by addition of 10 g of callus into 50 ml of the different media (RD1-RD6—see below). All cell lines that were successfully established on solid media developed a homogenous cell suspension in the same media combinations but lacking a gelling agent. The addition of 70 mg/l DTT or 150 mg/l of either ascorbic acid or citric acid improved growth and inhibited cell necrogenesis of berry derived suspension culture. All explant types were successfully utilized for the establishment of liquid cultures. Cultures were routinely subcultured every 7-10 days to fresh growing media.

Additional *Vitis* species that were introduced in order to establish berry derived callus cell lines: The following *Vitis* species were cultured using the above mentioned protocol:

*Vitis silvestris, V. muscadinia, V. rotundifolia, V. riparia, V. shuttleworthii, V. lubrisca, V. daviddi, V. amurensis, V. romanelli, V. aestivalis, V. Cynthiana, V. cineria, V. palmate, V. munsoniana, V. cordifolia*, Hybrid A23-7-71, *V. acerifolia, V. treleasei, V. betulifolia*.

The efficiency of callus production of *Vitis vinifera* grape cross sections, grape skins and grape seeds is exemplified in Table A hereinbelow.

TABLE A

| Explant type | Number of plate cultured | % of plated producing calli | Type of callus produced |
|---|---|---|---|
| Berry disks | 537 | 64 | Light red to purple |
| Skin | 498 | 51 | Dark red to purple |
| Seed coat | 428 | 49 | Red brownish |

The efficiency of production of the different callus 'types' from some of the *Vitis* species utilized in this study is summarized in Table B hereinbelow.

TABLE B

| *Vitis* species | Explant type | Average efficiency of callus production (%) | Callus type | Optimal Media |
|---|---|---|---|---|
| *Muscadinia* (*rutondifolia*) | B SC, S | 43 | Dark red | RD1 |
| *shuttleworthii* | B SC, S | 29 | Red | RD3 |
| *aestivalis* | B SC, S | 36 | Dark red | RD2 |
| Hybrid A23-7-71 | B SC, S | 19 | Red-brownish | RD6 |
| *amurensis* | B SC, S | 51 | Red | RD1 |

(B—Berry disk, SC—Seed coat, S—Skin)

Stage 1: Erlenmeyer, Shake Flasks

Red Grape Cells are grown in suspension under continuous fluorescent light (1000 lx) at 25±5° C., in 1 liter Erlenmeyer flasks on an orbital shaker. The growing medium contains Gamborg B5 medium and vitamins and is supplemented with 250 mg/l casein hydrolizate, 2-4% sucrose, 100 mg/l Myo-inositol, 0.2 mg/l Kinetin and 0.1 mg/l NAA (1-naphthaleneacetic acid), 25-45 mM $KNO_3$, 1-15 mM $MgSO_4$ or 5-35 mM $MgNO_3$ and 1 mM $NaH_2PO_4$ (pH 5.8). The cells are sub-cultured every 6-11 days.

Stage 2: Small Scale Bioreactor

Small scale bioreactor culturing is performed by inoculating a 7 to 16 old day cell suspensions grown in the Erlenmeyer of stage 1 into a 4-8 liter disposable bioreactor at 25±5° C. The cells are grown in the suspension under continuous fluorescent light (1000 lx) in a growing medium containing enriched Gamborg B5 salt and vitamins medium supplemented with 250 mg/l casein hydrolizate, 2-4% sucrose, 100 mg/l Myo-inositol, 25-45 mM $KNO_3$, 1-15 mM $MgSO_4$ or 5-35 mM $MgNO_3$ and 1 mM $NaH_2PO_4$, 0.2 mg/l Kinetin and 0.1 mg/l NAA (1-naphthaleneacetic acid) (pH 5.4-5.8). The cells are sub-cultured every 9-16 days.

Stage 3: Large Scale Bioreactor

The cell suspension grown in a small scale bioreactor are inoculated into a 30-50 liter disposable bioreactor. The cells are grown in a suspension under continuous fluorescent light (1000 lx) at 25±5° C. The growing medium containing enriched Gamborg B5 salt and vitamins medium supplemented with 250 mg/l casein hydrolisate, 2-4% sucrose, 100 mg/l Myo-inositol, 25-45 mM $KNO_3$, 1-15 mM $MgSO_4$ or 5-35 mM $MgNO_3$ and 1 mM $NaH_2PO_4$, 0.2 mg/l Kinetin and 0.1 mg/l NAA (1-naphthaleneacetic acid) (pH 5.4-5.8). The cells are sub-cultured every 12-30 days.

Stage 4: Larger Scale Bioreactor

The cell suspension grown in a small or large scale bioreactor are inoculated into a 300-1000 liter disposable bioreactor. The cells are grown in a suspension under continuous fluorescent light (1000 lx) at 25±5° C. The growing medium contains enriched Gamborg B5 salt and vitamins medium supplemented with 250 mg/l casein hydrolisate, 2-4% sucrose, 100 mg/l Myo-inositol, 25-45 mM $KNO_3$, 1-15 mM $MgSO_4$ or 5-35 mM $MgNO_3$ and 1 mM $NaH_2PO_4$, 0.2 mg/l Kinetin and 0.1 mg/l NAA (1-naphthaleneacetic acid) (pH 5.4-5.8).

Stage 5: Harvesting

The cells are harvested once they reach a cell biomass of 10% to 70% (w\v). The harvested cells are dried to produce a fine pink-purple powder, with a typical composition, taste and odor.

Example 2

The Effect of Medium Composition and Bioreactor Design on the Level of Resveratrol in Red Grape Cells Grown in Large Scale Bioreactor 2.1 Medium Composition Experiment 1: The Effect of Medium Composition on the Amount of Resveratrol in Red Grape Cells Grown in Erlenmeyer Shake Flask.

Red Grape Cells were grown in Erlenmeyer shake flask as described on Example 1, stage 1, in different medium compositions: MS, WP, WP+Casein, Gamborg B5. The results presented in Table 1, demonstrate that cells grown in the presence of Gamborg B5 medium produce approximately 4 to 15 fold higher resveratrol levels than cells grown in the presence of MS, WP and WP+Casein medium.

TABLE 1

| Medium* | Fresh weight g/L | Resveratrol mg/L | Total Polyphenols mg/L |
|---|---|---|---|
| MS** | 125 | 13.1 | 143.4 |
| WP*** | 132 | 24.6 | 208.9 |

TABLE 1-continued

| Medium* | Fresh weight g/L | Resveratrol mg/L | Total Polyphenols mg/L |
|---|---|---|---|
| WP + Csaein hydrolizate | 152 | 7.7 | 126.2 |
| Gamborg B5 | 166 | 141 | 735 |

*The data are the mean of at least two experiments
**MS-Murashige and Skoog medium (Toshio Murashige and Folke K. Skoog in 1968)
***WP—Woody Plant Medium (WP) (Lloyd and McCown, 1981)

Experiment 2: The Effect of Medium Composition on the Growth and Resveratrol Level in Red Grape Cells Grown in a Large Scale Disposable Bioreactor.

Red Grape Cells were grown in large disposable bioreactor as described on Example 1 stage 3, in different medium compositions.

Red Grape Cells were grown in two types of medium: Gamborg B5 medium and enriched Gamborg B5. As revealed in Table 2 below, supplementation of Gamborg B5 medium with high level of magnesium, phosphate and nitrates or sulfate salts ($KNO_3$, $MgSO_4$, $MgNO_3$, $NaH_2PO_4$) resulted in a higher Red Grape Cells biomass in comparison to the biomass obtained in the presence of non-enriched Gamborg B5 medium.

TABLE 2

Growth of Red Grape Cells in scale up bioreactors in Gamborg B5 and enriched Gamborg B5 medium

| Medium composition | Fresh weight gram/L |
|---|---|
| Enriched Gamborg B5 ($KNO_3$, $MgSO_4$, $MgNO_3$) | 240 |
| Gamborg B5 | 110 |

*The data are the mean three experiments

In addition, the effect of medium composition on resveratrol and total polyphenols levels in Red Grape Cells grown in a large scale disposable bioreactor was examined. The cells were grown in WP medium and in Gamborg B5 medium containing different concentrations of magnesium, nitrates and phosphates ($KNO_3$, $MgSO_4$, $MgNO_3$, $KNO_3$ and $NaH_2PO_4$, accordingly) salts. Table 3 demonstrates that these salts are required for production of high levels of polyphenols and of resveratrol, in particular when added to the enriched Gamborg B5 medium. As opposed in WP medium, the level of total polyphenols and resveratrol is very low.

Figure 4:
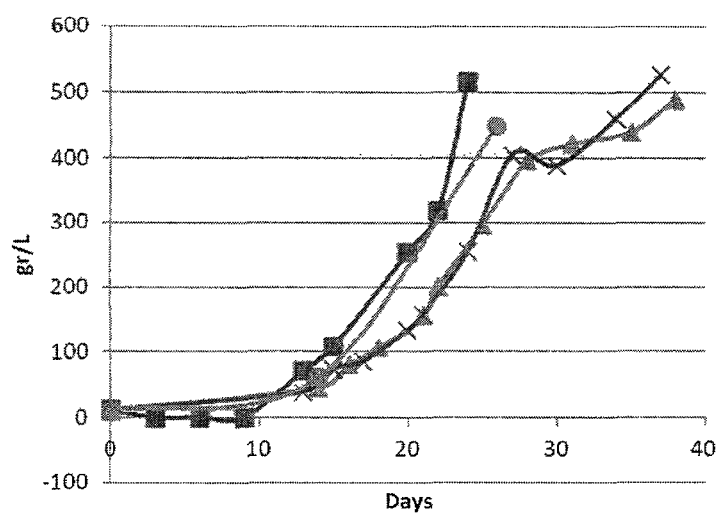
FIG. 4 presents growth curves of four different batches of Red Grape Cells grown in a large scale disposable bioreactor in enriched Gamborg B5 medium. The cells undergo exponential growth yielding a 500 gr/l fresh biomass at day 20 up to 40. These cells continue to grow and can reach a higher biomass.

FIG. 4 presents growth curves of Red Grape Cells grown in a large scale disposable bioreactor in enriched Gamborg B5 medium. The cells undergo exponential growth yielding a 500 gr/l fresh biomass at day 20 up to 40. These cells continue to grow and can reach a higher biomass.

TABLE 3

Levels of Resveratrol, and total polyphenols in RGC grown in different mediums with different levels of salts, in large scale bioreactors (50 L)

| Medium*** | Treatment | | | | Resveratrol µg/mg | Total Polyphenols eq. Epicatechin µg/mg |
|---|---|---|---|---|---|---|
| | $MgSO_4$ mM* | $MgNO_3$ mM* | $NaH_2PO_4$ mM* | $KNO_3$ mM* | | |
| **B5 | | (5-5.7) | 2 (1) | 50 (25) | 18.0-25.3 | 41.4-54.1 |
| **B5 | | (5.5-15) | 2 (1) | 50-70 (25-45) | 12.4-22.5 | 31.6-63.5 |
| **B5 | | (20-25) | 2 (1) | 70 (45) | 12.7-16.8 | 35.2-44.1 |

TABLE 3-continued

Levels of Resveratrol, and total polyphenols in RGC grown in different mediums with different levels of salts, in large scale bioreactors (50 L)

| | Treatment | | | | | Total Polyphenols eq. |
|---|---|---|---|---|---|---|
| Medium*** | $MgSO_4$ mM* | $MgNO_3$ mM* | $NaH_2PO_4$ mM* | $KNO_3$ mM* | Resveratrol μg/mg | Epicatechin μg/mg |
| **B5 | 9.1 (8) | (5) | 2 (1) | 50 (25) | 13.5-18.4 | 29.8-67.4 |
| **B5 | 9.1 (8) | | 2 (1) | 50 (25) | 15.0-20.3 | 42.6-48.1 |
| **B5 | 13.1 (12) | | 2 (1) | 50 (25) | 14.0-31.3 | 51.4-117.9 |
| **B5 | 16.1 (15) | | 2 (1) | 50 (25) | 13.2-18.5 | 34.0-53.0 |
| **B5 | 13.1 (12) | (25-35) | 2 (1) | 50 (25) | 6.2-16.8 | 40.5-44.1 |
| ****WP | | | | | 1.0 | 15.2 |

Note- The values in part present as a range
*Numbers in bracket describe additional concentrations of minerals added to Gamborg B5
**The data are the mean of at least of three experiments.
***The data are the mean of at least ten experiments.
****McCown's Woody Plant medium (Lloyd and McCown, Proc. Int. Plant Prop. Soc. 30: 421, 1981

Experiment 3: Consistency of Resveratrol and Total Polyphenols Levels in RGC Grown in Different Growth Stages from Erlenmeyer Shake Flask to Large Scale Bioreactor Red Grape Cells were grown in different scale stages from Erlenmeyer shake flask to a large scale disposable bioreactor in the presence of enriched Gamborg B5 as described on Example 1, stages 1 to 4.

The results in table 4 show that Red Grape Cells grow well in Erlenmeyer and synthesized high amount of resveratrol and total polyphenols. When the cells were grown in either 50 liter, 300 to 1000 liters scale in disposable bioreactors, a higher growth rate achieved in comparison to the growth in an Erlenmeyer flask as revealed by fresh and dry weight of the cells, see the data in Table 4. In all sizes of the scale up bioreactors, the fresh weight was above 230 g/l (Table 4) as compared to 166 g/l in Erlenmeyer. Moreover, the level of total polyphenols as well as of resveratrol in the enriched medium, in large scale disposable bioreactors was higher than the level obtained in the Erlenmeyer flask 901 mg/l and 200 mg/l, respectively (Table 4). In contrast to observations made by others, this is the first time to demonstrate successful growth of fruit plant cells in large scale disposable bioreactor with high level of resveratrol and polyphenols production.

TABLE 4

Resveratrol and total polyphenols level in RGC grown in shake flask and different scale stages*

| Experimental set-up | Fresh weight gram/L | Dry weight gram/L | Resveratrol mg/L | Total Polyphenols mg/L |
|---|---|---|---|---|
| Erlenmeyer flask | 166 | 8.2 | 141 | 735 |
| Small scale disposable bioreactor | 102 | 15 | 179 | 1287 |
| Large scale up 50 liters disposable bioreactor | 313 | 13 | 205 | 1087 |
| Larger scale disposable bioreactor 300-1000 liters | 242 | 15 | 200 | 901 |

*The data are the mean of at least of three experiments.

Experiment 4: The Effect of Casein Hydrolyzate Addition on Resveratrol and Total Polyphenols Level in Red Grape Cells Grown in Large Scale Disposable Bioreactor Red Grape Cells were grown in a large scale disposable bioreactor in the presence of enriched Gamborg B5 as described in Example, 1 stage 3.

As can be seen in Table 5, the levels of resveratrol and total polyphenols in Red Grape Cells were similar when grown in disposable large scale bioreactor in enriched medium with or without 250 mg/l casein hydrolisate.

TABLE 5

| Medium | Total resveratrol gr/kg dry powder | Total Polyphenols gr/kg dry powder |
|---|---|---|
| Without Casein* | 13.6 ± 2.2 | 45.4 ± 6.0 |
| With casein hydrolizate | 13.1 ± 1.6 | 63.2 ± 10.2 |

*The data are the mean of three experiments

Experiment 5: The Effect of Plant Hormones Addition on Resveratrol and Total Polyphenols Levels on Red Grape Cells Grown in Large Scale Disposable Bioreactor.

Red Grape Cells were grown in a large scale disposable bioreactor in enriched Gamborg B5 as described on Example 1, stage 3. As can be seen in Table 6, the levels of resveratrol and total polyphenols production in Red Grape Cells were similar when grown in disposable large scale bioreactor with or without 0.5 mg/l NAA and 0.2 mg/l kinetin (Table 6).

TABLE 6

| Medium | Total resveratrol mg/kg | Total Polyphenols mg/kg |
|---|---|---|
| Average ± SD With hormones* | 12.0 ± 0.6 | 60.5 ± 3.0 |
| Average ± SD Without hormones* | 13.1 ± 1.6 | 63.2 ± 10.19 |

*The data are the mean of three experiments

Experiment 6: The Effect of Sucrose Concentration on Red Grape Cells Grown in Large Scale Disposable Bioreactor.

Red Grape Cells were grown in large disposable bioreactor (50 liter) as described on Example 1 stage 3, in enriched Gamborg B5 medium with different sucrose concentrations.

Red Grape Cells were grown in enriched Gamborg B5 mediums which contain 2, 3, 4 and 6% sucrose. As revealed in Table 6A below, optimum cell growth and biomass is achieved when cells are grown with 2 to 4% sucrose (143 to 260 gram/L). Higher sucrose concentration such as 6% sucrose inhibits cell growth by 10 fold (24 gram/L).

TABLE 6A

| Medium composition | Fresh weight gram/L |
|---|---|
| Enriched Gamborg B5 2% sucrose | 221 |
| Enriched Gamborg B5 3% sucrose | 260 |
| Enriched Gamborg B5 4% sucrose | 143 |
| Enriched Gamborg B5 6% sucrose | 24 |

Experiment 7: The Effect of the Bioreactor Configuration, Design and Structure on Resveratrol and Total Polyphenols Levels in Red Grape Cells Grown in Large Scale Disposable Bioreactor The effect of two mediums, IM1 medium and Gamborg B5 enriched with magnesium, phosphate and nitrates salts on the amount of resveratrol produced by the cells was assessed in 20 L bioreactors made from a sterilized, disposable, transparent plastic container and further compared to data published in A. Decendit (1996) Biotechnology Letters, where cells were grown in IM1 medium in a 20 L glass container.

The results demonstrated that Red Grape Cells grown in IM1 medium in a disposable bioreactor produced 93 mg/l of resveratrol (Table 7) which is approximately 3 fold higher resveratrol than the level produced in stirred glass bioreactor using the same medium (Decendit). Moreover, significant high level of resveratrol, 387 mg/l, was produced when these cells were grown in enriched Gamborg B5 in disposable bioreactor (Table 7).

TABLE 7

The effect of bioreactor type and medium composition on Resveratrol levels produced by Red Grape cells

| Medium | Bioreactor Type | Resveratrol mg/L |
|---|---|---|
| Enriched Gamborg B5 Medium** | Disposable | 387 |
| IM1 Medium** | Disposable | 93 |
| IM1 Medium* | Stirred glass | 30 |

*IM1 Medium-Ref. article A. Decendit (1996) Biotechnology Letters
**The data are the mean of at least of three experiments Further, the combination of specific medium composition that contains enriched Gamborg B5 and design disposable bioreactor induced the cells to produce 10 to 12 fold more resveratrol than the level that was produced in IM1 medium and stirred glass bioreactor and 4 fold more than in cell grown in IM1 medium in disposable bioreactor (table 7).

These results show that both the bioreactor type and the medium composition are required for maintaining high level of resveratrol in RGC produced in a bioreactor of 20 L or more.

Example 3

Composition:

Both red and purple grapes contain powerful polyphenols, antioxidants and resveratrol, which helps to prevent both the narrowing and hardening of the arteries. Increasing research has shown that resveratrol found in red and purple grapes and ultimately in red wine—influences important metabolic pathways in the body and may benefit our health. They do, however, have a very high sugar content and should therefore be eaten in moderation.

The composition of Red Grape Cells grown in large scale disposable bioreactor is unique.

The chemical composition of Red Grape Cells is comparable to grapes grown using standard agricultural practices except from the level of the sugar and the resveratrol.

Experiment 8: Lower Level of Total Sugars, Glucose and Fructose in Red Grape Cells Grown in Large Scale Disposable Bioreactor Compare to Red Grape Grown in the Vineyard.

The amount of total sugars, glucose and fructose in Red Grape Cells that were grown in a large scale disposable bioreactor as described on Example 1, stages 3 and 4 in enriched Gamborg B5 is 25 to 50 fold lower compare to the level of these sugars from deferent types of red grapes grown by agriculture means (table 8).

TABLE 8

Sugars Comparison of sugars level between Red Grape Cells grown in large scale disposable bioreactor and Agricultural Red Grapes
(Fresh Weight)
(gr/100 gr)

A.

| Sugars (%) | RGC Batches | | | | | | | |
|---|---|---|---|---|---|---|---|---|
| | 1 | 2 | 3 | 6 | 16 | 17 | 18 | Range |
| Glucose | 0.39 | 0.54 | 0.54 | 0.55 | 0.33 | 0.36 | 0.23 | 0.2-0.55 |
| Fructose | 0.311 | 0.42 | 0.46 | 0.36 | 0.43 | 0.73 | 0.25 | 0.31-0.73 |
| Total sugars | 0.7 | 0.96 | 1.0 | 0.91 | 0.76 | 1.1 | 0.48 | 0.48-1.1 |

B.

| | Agricultural Red Grapes | | | | |
|---|---|---|---|---|---|
| Sugars (%) | Sample 1 | Sample 2 | Sample 3 | Sample 4 | Range |
| Glucose | 7.47 | 10.71 | 11.32 | 8.69 | 7.4-11.3 |
| Fructose | 7.57 | 14.67 | 11.39 | 7.74 | 7.5-14.6 |
| Total sugars | 15 | 25.4 | 22.71 | 16.4 | 15-25.4 | sample 1 - Agricultural Table Red Grape (Israel)-Red grape used for eating
Sample 2 - Wine Red Grape 1 (Israel) Cabernet- Red grape used for making wine
Sample 3 - Wine Red Grape 2 (Israel) Cabernet- Red grape used for making wine
Sample 4 - Wine Red Grape 1 (South Africa) Cabernet-Red grape used for making wine Experiment 9: Level of Total Polyphenols and Resveratrol Composition of Red Grape Grown in Large Scale Disposable Bioreactor.

The levels of total polyphenols in Red Grape Cells are similar to the amounts in red grapes grown in the field with the exception of resveratrol, which is present is 40 to 800 fold higher (Tables 9 and 10). The level of resveratrol in five batches of Red Grape Cells grown in large scale disposable bioreactor as described on Example 1, stages 3 and 4, is in the range of between 726 to 916 mg/kg fresh weight compared to 0-42.5 mg/kg in agricultural red grapes (Table 9). The level of resveratrol in the dry powder of Red Grape Cells after the drying process ranges from 6000 to 31000 mg/kg powder (Table 10).

Method: The levels of polyphenolics and of Resveratrol in Red Grape Cells were analyzed using HPLC coupled with UV/VIS detection at 280, 520 and 306 nm.

TABLE 9

Phenolic Content Composition between Red Grape Cells
and Agricultural Red Grapes
(mg/kg fresh weight)

| | Agricultural Red Grapes | | | | | |
|---|---|---|---|---|---|---|
| | Sample 1 | Sample 2 | Sample 3 | Sample 4 | Sample 5 | Range |
| Total Polyphenols | 727 | 4204 | 2940 | 2595 | 2655 | 727-4204 |
| Tannins (PACS) | 2389 | NT | NT | 5088 | 3069 | 2389-5088 |
| Resveratrol | ND | ND | ND | 42.5 | ND | 0-42.5 |

| | RGC Batches | | | | | |
|---|---|---|---|---|---|---|
| | 11 | 12 | 13 | 14 | 15 | Range |
| Total Polyphenols | 2333 | 2467 | 3133 | 2533 | 2600 | 2333-2600 |
| Tannins (PACS) | 2400 | 1867 | 3133 | 1840 | 2933 | 1840-3133 |
| Resveratrol | 813 | 916 | 906 | 866 | 726 | 726-916 |

ND—Not Detected,
NT—Not Tested
Sample 1- Agricultural Table Red Grape (Israel)-Red grape used for eating
Sample 2 -Wine Red Grape 1 (Israel) Cabernet- Red grape used for making wine
Sample 3 -Wine Red Grape 2 (Israel) Cabernet- Red grape used for making wine
Sample 4-Wine Red Grape 1 + Wine Red Grape 2 (Israel) Cabernet-Red grape used for making wine
Sample 5-Wine Red Grape 1 (South Africa) Cabernet-Red grape used for making wine

TABLE 10

Resveratrol and Total Polyphenolic compounds content
in Red Grape Cells

| Polyphenol compounds | Red Grape Cells batches | | | | | | | | | | |
|---|---|---|---|---|---|---|---|---|---|---|---|
| | 1 | 2 | 3 | 4 | 5 | 6 | 17 | 18 | 7 | 8 | Range |
| Total Polyphenols | 83 | 30 | 43 | 60 | 101 | 68 | 45.7 | 46.0 | 29.3 | 43 | 29-101 |
| Resveratrol | 31.3 | 20.4 | 13.6 | 24 | 18.1 | 14 | 17.6 | 16.8 | 14 | 6.3 | 6-31 |

(results in gr/kg dry powder)

Example 4

Effect of Cultured Grape Cells in In Vivo Carrageenan-Induced Paw Oedema Rat Model The aim of the present study was to evaluate the in vivo anti-inflammatory activity of RGC (Red Grape Cells) made according to the large scale process of the invention in an acute inflammation model in rats so as to verify the efficiency of the cells produced according to the invention. One of the experimental model most widely used to study acute inflammation in rodents is that based on the intraplantar administration of carrageenan.

The study assessed the efficacy of the RGC by two methods:
1. Paw volume measurements
2. Inflammatory nociception in freely moving rats Materials and Methods:
Red Grape Cells (RGC) prepared according to example 1.
RGC was administered orally at dose of 400 mg/kg body weight (2 ml/40 mg) as a suspension in sterile drinking water, 2 h before carrageenan injection.
RGC Composition: The amounts of polyphenols and resveratrol injected to each rat were 14 and 4.8 mg, respectively (3.5 mg polyphenols per 100 mg RGC and 1.2 mg resveratrol per 100 mg RGC).

Carrageenan induced rat paw edema: Rats were divided into three groups of eight rats in each group. The rats in all groups were injected with 1% carrageenan (0.1 mg/paw) or sterile saline (0.9% NaCl) into the sub plantar tissue of left hind paw of each rat.

The Following Tests were Performed:

Paw Volumes Measurements
Carrageenan injected paw volumes were measured hourly just before carrageenan injection 0 and 1, 2, 4 hours after injection using caliper.
The paw dimensions were measured in two axes and paw volume was calculated. Paw edema volume in this model was an indication of the inflammation severity.
For each time point, the change in paw volume was calculated either by subtracting the baseline paw volume or as % of baseline paw volume.

Hot Plate Method for Measuring Inflammatory Nociception in Freely Moving Rats
The hot plate method was used to determine inflammatory nociception in freely moving rates. After inducing edema and treatment with either vehicle, indomethacin or RGC preparation, the rats were placed on a hot plate maintained at a temperature of 55±0.5° C. The latency to flick the hind paw or lick or jump from the hot plate in comparison to its baseline was considered as the reaction time. The reaction time was noted at 1, 2, and 4 hours after injection. In absence of response, a 30 seconds cut off is used to prevent tissue damage.

Group Allocation:
Vehicle control (1M) group: The control rats received sterile drinking water (vehicle), 2 h before carrageenan injection.
Positive control group ("2M"): the rats in the positive control group received 2 mg/kg body weight of indomethacin 2 h before carrageenan injection.
Test group ("3M"): the rats were administered orally with RGC at dose of 400 mg/kg body weight (2 ml/40 mg RGC) as a suspension in sterile drinking water, 2 h before carrageenan injection.

Results
Paw Swelling:
FIG. 1 shows the results of paw edema (volume %) in rates treated with RGC preparation, indomethacin and water as a control. Statistical analysis was carried out using two-way ANOVA for repeated measures, followed by Bonferroni post hoc tests. Comparison of control group (1M) to positive control group (2M) showed statistically significant difference at 2 and 4 h (p<0.001). Comparison of control group to RGC-preparation (3M) group showed statistically significant difference at 2 and 4 hours (p<0.001).

As shown in FIG. 1, paw swelling was reduced when the rats were treated with RGC preparation, at least to the level of the positive control, after 1 or 2 hours. Furthermore, after 4 hours the rats treated with RGC preparation demonstrated even a larger reduction in paw swelling then the control.

Figure 2:
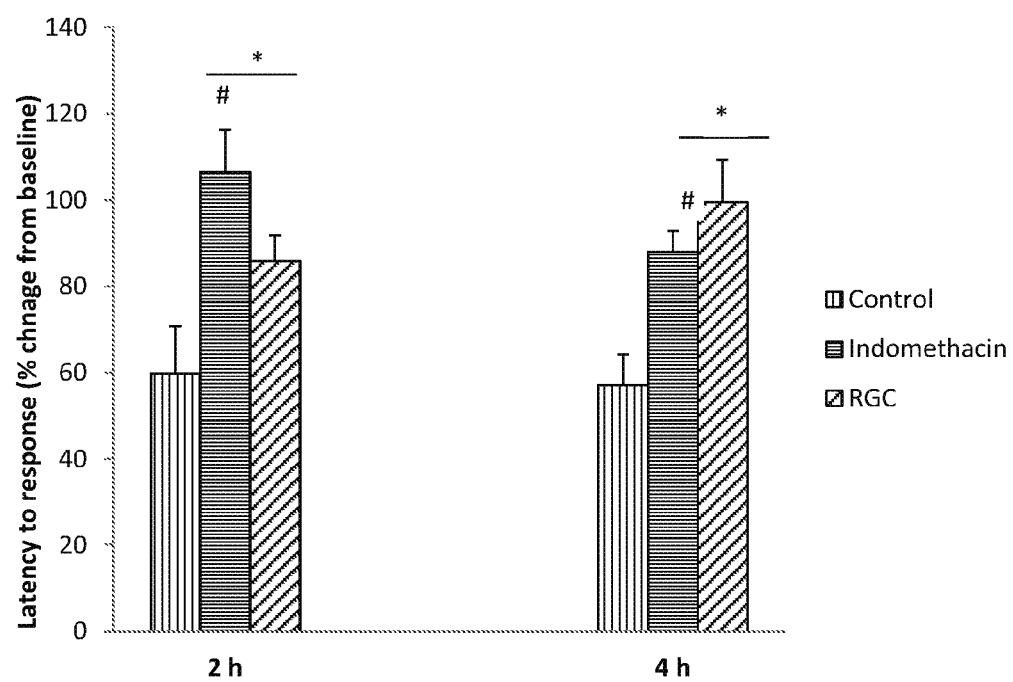
FIG. 2 shows the distribution of group's hyperalgesic effect measured by Hot Plate during the study (the results are expressed as "Hot plate latency, % from baseline" as a function of time). Statistical analysis was carried out using two-way ANOVA for repeated measures, followed by Bonferroni post hoc tests. Comparison of control group (1M) to positive control group (2M) showed statistically significant difference at 2 and 4 h ($p<0.05$-$0.01$). Comparison of control groups RGC (3M) showed statistically significant difference at 4 h ($p<0.01$).

Inflammatory Nociception FIG. 2 shows the group's hyperalgesic effect following treatment with RGC preparation, indomethacin and water as a control. Statistical analysis was carried out using two-way ANOVA for repeated measures, followed by Bonferroni post hoc tests. Comparison of control group 1M to positive control group 2M showed statistically significant difference at 2 and 4 h (p<0.05-0.01). Comparison of control groups CGC (3M) showed statistically significant difference at 4 h (p<0.01).

As can be seen in FIG. 2, vehicle treated control group (1M) (received sterile drinking water) showed a significant increase in the latency delta (time) to the thermal stimulus, 2 and 4 hours after carrageenan injection. This was evidence by the decrease in reactivity to the thermal plantar stimulation of the rats in this group.

Figure 3:
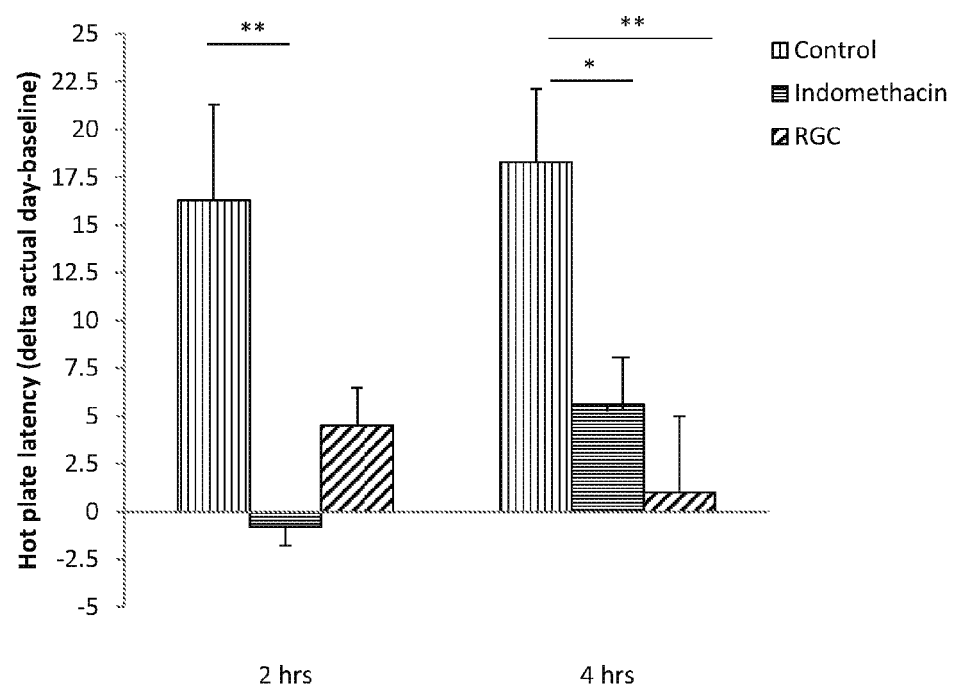
FIG. 3 shows the distribution of group's hyperalgesic effect measured in Hot Plate Test (the results are expressed as "Hot plate latency delta, baseline-actual time" as a function of time). Statistical analysis was carried out using two-way ANOVA for repeated measures, followed by Bonferroni post hoc tests. Comparison of control group (1M) to positive control group (2M) showed statistically significant difference at 2 and 4 h (p<0.05-0.01). Comparison of control groups and RGC-treated mice (3M) showed statistically significant difference at 4 h (p<0.01).

As can be seen in FIG. 3 positive control group (indomethacin-treated rats, 2M) showed a significant decrease in the latency delta of response to the thermal stimulus, 2 and 4 hours after carrageenan injection compared to the vehicle control.

The RGC treated rats (3M) showed a decrease in the latency delta response to the thermal stimulus which, four hours after carrageenan injection, was statistically significant compared to vehicle treated controls.

In conclusion, the results demonstrated in this example show that the paw edema and behavioral hyperalgesia associated with carrageenan-induced hind paw inflammation in rats were positively attenuated by the oral administration of RGC made according to the process described in example 1 being indicative of the anti-inflammatory effect of the RGC preparation is restored even in RGC that are prepared in a large scale process. This is in strike contrast to a study described by Gentilli et al (2001) using the same carrageenan induced hyperalgesia model. The study showed that high concentration of resveratrol (50 mg/kg body weight as opposed to an equivalent of 6 mg/kg body weight used in the current study) administered to rats prior to carrageenan injection into the paw failed to reduce paw edema.

Example 5

Tests on Animals

40 Sprague-Dawley (SD) male rats, weight 250±25 grams, were obtained from Harlan Laboratories Ltd., Jerusalem, Israel. The rats were housed in regular cages situated in an animal room at 22° C. with a 14-hour light/10-hour dark cycle. The rats were maintained on a standard rat chow diet and given tap water to drink ad libitum, for an acclimation period of five days. Following the acclimation period, the rats were switched to a fructose-enriched diet (Teklad-Harlan, Madison, USA) consisting of 21% protein, 5% fat, 60% carbohydrate, 0.49% sodium, and 0.49% potassium, and were divided to four groups (10 rats in each group).

All SD rats were fed a high fructose diet for five weeks. For part of the rats (30 rats) different doses (200, 400 and 800 mg/Kg/day) of RGC were added directly to the rat chow after three weeks of being fed with the high fructose diet.

Body weight, systolic BP, plasma triglyceride, insulin and adiponectin levels were measured at baseline and after three and five weeks of diet, the first and the second measurements being before the RGC supplementation to the 30 rats and the third, after five weeks (namely, after two weeks of RGC supplementation period). At the beginning of the study and after three and five weeks of diet, 20 rats (10 rats of the control group and 10 rats with supplementation of 400 mg RGC) were housed in metabolic cages for analysis of urinary sodium excretion.

Blood Pressure Measurements

Systolic blood pressure (BP) was measured by the indirect tail cuff method, using an electrosphygmomanometer and pneumatic pulse transducer (58500 BP Recorder, UGO BASILE, Varese, Italy). The measurements were performed while the rats were kept in a temperature-regulated rat holder. The mean of five consecutive readings was used for systolic BP determination.

Laboratory Measurements

Blood samples were taken from a retro-orbital sinus puncture under light anesthesia with isoflurane, from all rats after five hours of fasting at the indicated time points (the first and the second measurements were performed before the RGC supplementation and the third, five weeks from the starting point (namely, after two weeks of RGC supplementation period).

Blood for plasma was collected in the presence of EDTA to prevent clotting and was kept on ice. Following centrifugation, plasma was separated and frozen at −80° C. until further analysis. Triglyceride levels were assayed with an automated analyzer of an enzymatic colorimetric reaction (Olympus AU 2700, Hamburg, Germany). Plasma insulin was assessed using I-125 RIA kit (INSIK-5, Diasorin, USA). Total plasma adiponectin concentrations were measured by adiponectin RIA kit (Cat. #MADP-60HK from Linco Research Inc., St. Charles, Mo.). Urinary sodium excretion rates were measured by automatic analyzer (Olympus An 2700; Olympus Diagnostics, Hamburg, Germany).

Results

Effect of RGC on Blood Pressure, Plasma Triglycerides, Insulin, Adiponectin, and Sodium Excretion.

Figure 5:
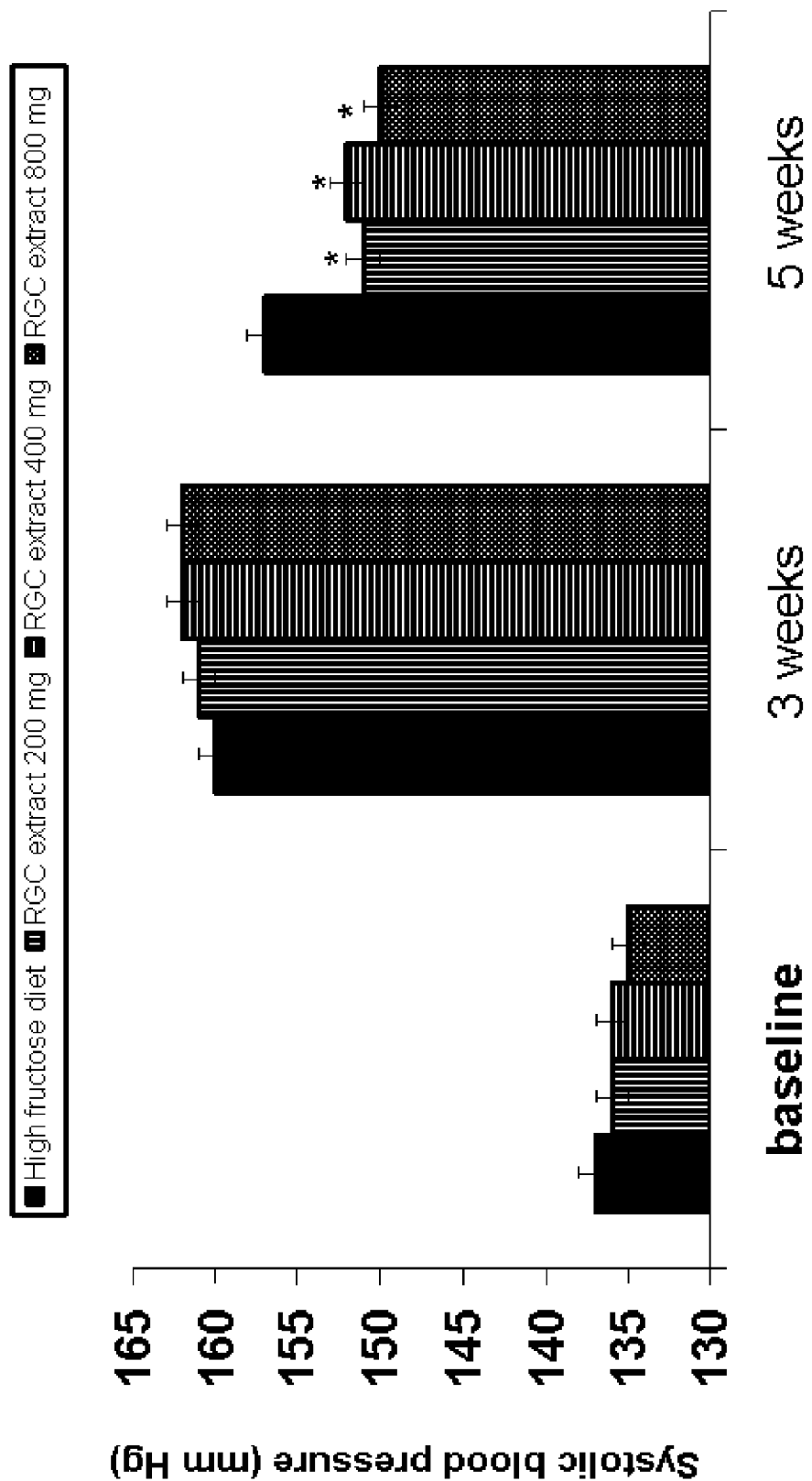
FIG. 5 represents the systolic blood pressure (BP) .vs. time in high fructose diet fed rats, with and without supplementation of different amounts of red grape cell (RGC), at baseline and after three and five weeks of diet.

Body weight gains were similar in rats fed with a high fructose diet with and without supplementation of RGC (Table 11). High fructose diet induced a significant rise in blood pressure, plasma triglycerides, insulin and adiponectin levels (FIG. 5, Table 4). Systolic BP increased by 19.1±1.1 mm Hg after five weeks of high fructose diet (p<0.001) from 137 mm Hg to 156 mm Hg. Supplementation of RGC attenuated BP rise induced by high fructose diet (FIG. 5) from 161±4.5 to 151 ±3.6 mmHg in the first group that received 200 mg/Kg/day of RGC, from 162±5 to 152±3 mmHg in the second group that received 400 mg/Kg/day of RGC and from 162±2.8 to 150±1.8 mm Hg in the third group that received 800 mg/Kg/day of RGC (p<0.05). Supplementation of RGC attenuated the level of triglycerides in the plasma from 234±14 to 171±12 mg/dL in the first group that received 200 mg/Kg/day of RGC, from 235±12 to 167±24 mg/dL in the second group that received 400 mg/Kg/day of RGC and from 219±31 to 142±21 mg/dL in the third group that received 800 mg/Kg/day. RGC attenuated the rise of plasma insulin levels induced by high fructose diet, from ±43.5 mg/dL in control group (fructose-enriched diet) to 33.9 ±2.6, 34.4±3.8 and 31.6±2.9 mg/dL in rat groups treated with RGC at doses of 200, 400 and 800 mg/Kg/day, respectively.

RGC had no consistent effect on adiponectin levels, as shown by adiponectin levels of 5.8±0.3 in the control group compared to 6.0+0.4, 4.5±0.2 and 5.4±0.5 in rat groups treated with RGC of doses of 200, 400 and 800 mg/Kg/day of RGC, respectively.

Baseline urinary sodium excretion was the same in rats either with or without supplementation of RGC (0.5±0.1 and 0.7±0.2 mmol/day, respectively, p=0.43). Urinary sodium excretion increased significantly after three weeks of high fructose diet and remained unchanged after supplementation of RGC (after 3 weeks, 3.5±0.2 and 2.3±0.3 mmol/day in rats without and with supplementation of RGC, respectively; p<0.05 for both, and after five weeks, 3.1±0.2 and 1.8±0.3 mmol/day, respectively; p=0.4 between groups).

TABLE 11

Body weight, Triglycerides, Insulin and adiponectin levels in the studied groups.

| | Fructose - enriched diet | Fructose -enriched diet with Supplementation of RGC for 2 weeks | | |
|---|---|---|---|---|
| | | 200 mg/Kg/day | 400 mg/Kg/day | 800 mg/kg/day |
| BodyWeight (grams) | | | | |
| baseline | 243 ± 11 | 255 ± 11 | 249 ± 8 | 245 ± 8 |
| 3 weeks | 344 ± 21 | 350 ± 21 | 351 ± 10 | 341 ± 11 |
| 5 weeks | 365 ± 24* | 377 ± 27* | 380 ± 12* | 348 ± 15* |
| triglycerides (TG) (mg/dL) | | | | |
| baseline | 91 ± 8 | 94 ± 8 | 106 ± 8 | 81 ± 5 |
| 3 weeks | 195 ± 18 | 234 ± 14 | 235 ± 12 | 219 ± 31 |
| 5 weeks | 200 ± 9* | 171 ± 12*# | 167 ± 24*# | 142 ± 21*# |
| Insulin (mg/dL) | | | | |
| baseline | 15.2 ± 1.5 | 22.7 ± 1.2 | 19.9 ± 1.4 | 16.7 ± 0.8 |
| 3 weeks | 37.6 ± 4.4 | 29.7 ± 1.8 | 30.0 ± 1.6 | 22.6 ± 1.3 |
| 5 weeks | 43.5 ± 1.9* | 33.9 ± 2.6*# | 34.4 ± 3.8*# | 31.6 ± 2.9*# |
| Adiponectin (mg/dL) | | | | |
| baseline | 3.8 ± 0.3 | 4.8 ± 0.2 | 4.9 ± 0.3 | 4.0 ± 0.2 |
| 3 weeks | 5.7 ± 0.3 | 6.3 ± 0.5 | 5.8 ± 0.2 | 5.4 ± 0.3 |
| 5 weeks | 5.8 ± 0.3* | 6.0 + 0.4 | 4.5 ± 0.2# | 5.4 ± 0.5* |

*$p < 0.05$ vs. baseline,
$p < 0.05$ vs. Fructose -enriched diet.

Example 6

Chemical Properties of RGC-RES Compared to RES from Other Sources and Human Bioavailability Properties of RGC-RES Materials and Methods Red Grape Cells (RGC) was prepared according to example 1. The resveratrol (RES) content of the RGC was determined by HPLC at 306 nm against a synthetic RES calibration curve.

LC/MS Analysis of RGC-RES

RGC powder was dissolved in 80% methanol. Liquid chromatography mass spectrometry (LC-MS) analysis of the sample was performed using an Accela LC system coupled with the Linear Trap Quadrupole (LTQ) Orbitrap Discovery hybrid FT mass spectrometer (Thermo Fisher Scientific Inc.) equipped with an electrospray ionization source. The mass spectrometer was operated in the negative ionization mode and the mass spectra were acquired in the m/z 150-2000.

Solubility Assay

RGC, synthetic resveratrol (S-RES; Sigma-Aldrich) and resveratrol extract from the plant *Polygonum Capsidatum* (plant-RES) were dissolved in 80% methanol to achieve 100% dissolution. Then, all RES sources were dissolved in water at pH 2 and pH 7 and the percentage of dissolution in water was compared to the dissolution in methanol. The RES in all samples was monitored at 306 nm, based on its characteristic absorption profile, and its concentration was determined by a calibration curve of resveratrol analytical standard.

Results

LC/MS

Figure 6A:
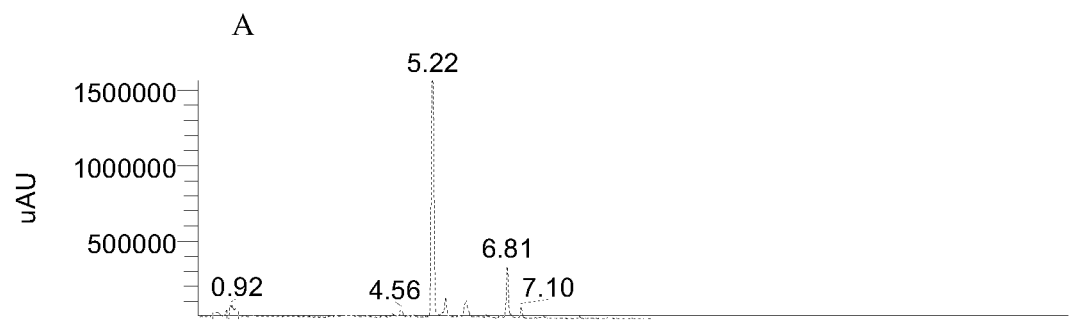
FIG. 6A is a UV chromatogram ($\lambda$=306 nm) and FIG. 6B is an extracted ion chromatogram (m/z −227.0701-227.0737) relating to the LC-MS analysis of resveratrol in RGC.
Figure 6B:
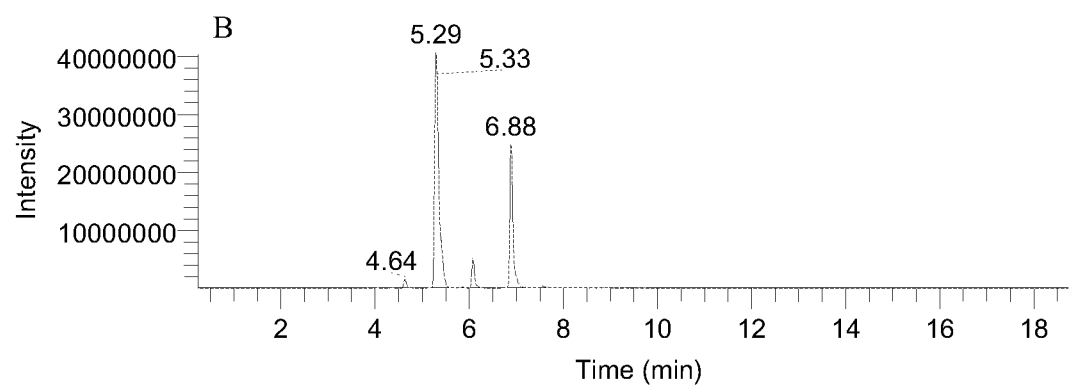
Figure 7:
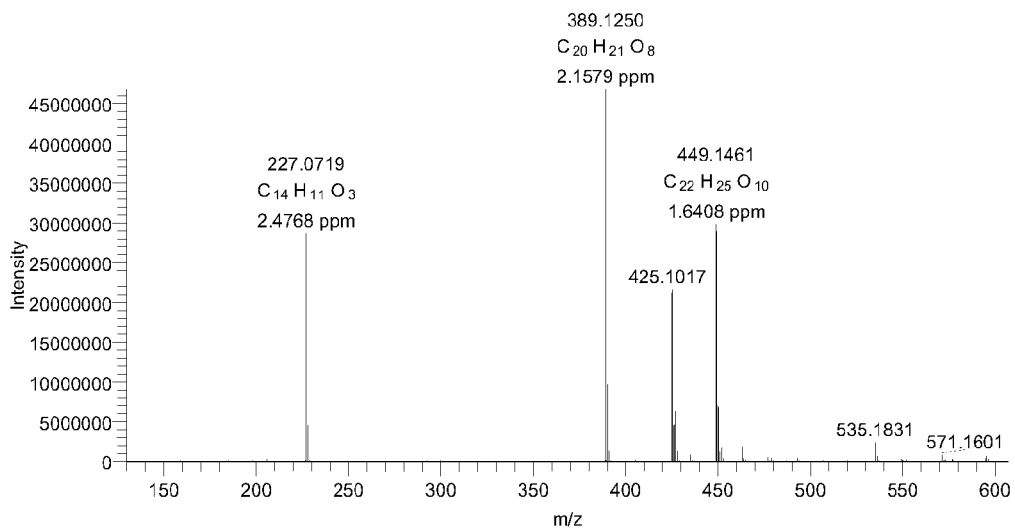
FIG. 7 present a negative ESI mass spectrum of a representative trans-RES glycoside (RT 4.64 min, m/z 389.1250), wherein resveratrol (m/z 227.0719) is an in source fragmentation product ion of m/z 389.1250.

The mass spectra in negative ion mode and representative LC/MS chromatogram for the RGC powder are shown in FIGS. 6A and 6B. LC-MS analysis detected four derivatives of resveratrol (m/z −227.0701-227.0737) in RGC, all of which show UV absorbance at 306 nm. Three of these derivatives were hexose glycosides of trans-RES isomers, detected at retention times of 4.6, 5.3 and 6.1 min. The fourth derivative was of trans-RES, detected at a retention time of 6.9 min (Table 12). The identity of the four derivatives was confirmed, as shown by ESI mass spectrum (FIG. 7).

TABLE 12

Identification of resveratrol derivatives in RGC

| [M − H]− | Calculated Atomic Composition | RT, min | Comment |
|---|---|---|---|
| 389.1250 | $C_{20}H_{21}O_8$ | 4.6 | Glycoside of trans-resveratrol |
| 389.1250 | $C_{20}H_{21}O_8$ | 5.3 | Glycoside of trans-resveratrol |
| 389.1250 | $C_{20}H_{21}O_8$ | 6.1 | Glycoside of resveratrol. Chromatographic separation was not complete but it also can be a derivative of cis-resveratrol (according to UV) |
| 227.0719 | $C_{14}H_{11}O_3$ | 6.9 | trans-Resveratrol |

Solubility

Figure 8:
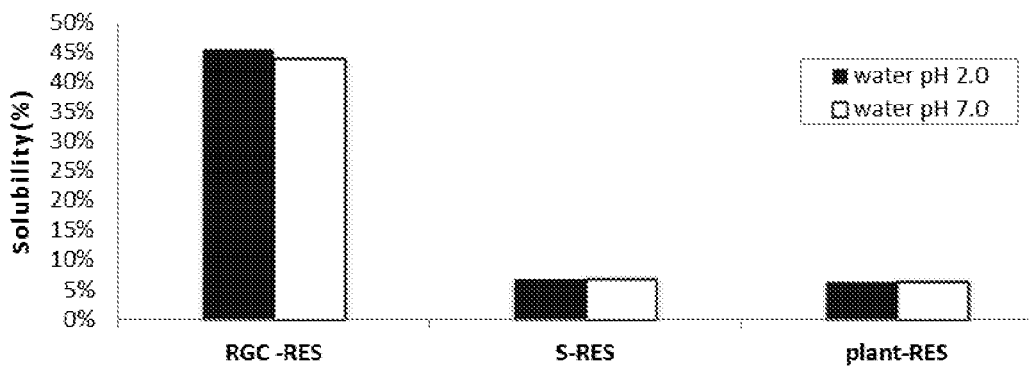
FIG. 8 provides results for the resveratrol (RES) solubility in water, comparing the solubility of RGC-RES, synthetic-RES and plant-RES.

The solubility of RGC-RES was compared to that of two trans-RES products: Synthetic-RES and plant *Polygonum Capsidatum*-RES. All three tested products were completely dissolved in 80% methanol solution. However, when the three RES products were dissolved in acidified water (pH=2), mimicking the stomach pH conditions as well as at pH 7.0, dissolution of RGC-RES was more than 6 fold higher, 44% for RGC-RES vs. 7% for the two other RES sources (FIG. 8).

Human Bioavailability Study

The study was a single dose randomized, crossover comparative pharmacokinetic study. Fifteen adult healthy fasting male subjects received the investigational product RGC (oral doses equivalent to 50 mg or 150 mg of trans-RES separated by at least 7 day washout periods. A Standard meal was served 4 hours post dosing. The study was performed in compliance with all rules and regulations of the Israel Ministry of Health (MOH) and according to the ICH GCP guidance. The protocol was approved by the Soroka University Medical Center IRB and included administering a single dose of 50 or 150 mg to each patient, followed by a 7 day washout, a second single dose, which is different than the first dose, so that a patient who initially received 50 mg will receive 150 for the second dose and vice versa. Fifteen healthy non-smoking male volunteers were recruited into the study. Volunteer eligibility criteria included ages of 18 to 55 years; BMI ≥19 and ≤30; Subjects were asked to refrain from RES-containing food, nutritional supplements or drinks and from all drugs including over the counter medications from 7 days before the first dosing, and throughout the entire study period.

Sample Collection and Management.

Venous blood samples were collected into $K_2EDTA$ containing tubes before (t0) and at 0.33, 0.67, 1, 1.5, 2, 2.5, 3, 4, 5, 6, 8, 10 and 12 hours post dosing. Blood samples were kept in an ice bath and immediately handled under yellow light.

Analysis of Resveratrol Content in Plasma

Sample preparation and LC-MS analysis for free and total RES in plasma samples was performed by PRACS Institute (Toronto, Canada). Plasma samples were liquid-liquid extracted and used for LC-MS/MS system for analysis. The lower limit of quantification (LLOQ) was 0.5 and 20 ng/mL for free and total RES, respectively. For the analysis of total RES, enzymatic hydrolysis and protein precipitation extraction was performed prior to LC-MS/MS analysis.

Pharmacokinetic Analysis

The following pharmacokinetic variables were calculated for free RES and for total RES (free and conjugated) using a noncompartmental pharmacokinetic approach: maximal plasma concentration (Cmax) and time of maximal plasma concentration (Tmax), average concentration over the total collection period, the area under the plasma concentration versus time curve (AUC) from time (0) to the last quantifiable concentration (Clast, above LOQ) by the trapezoidal method.

LDL Oxidation Assay

LDL Preparation: LDL was separated from plasma of healthy normolipidemic volunteers, by discontinuous density gradient ultracentrifugation.

Copper ion-induced LDL oxidation: LDL (100 mg of protein/mL) was incubated for 10 minutes at room temperature with increasing concentrations of grape powder ethanolic extract in each experiment. $CuSO_4$ was added and the tubes were incubated for 2 hours at 37° C. At the end of the incubation, the extent of LDL oxidation was determined by measuring the generated amount of thiobarbituric acid reactive substances (TBARS) and of lipid peroxides (PD).

Lipid Peroxidation assay: The extent of LDL oxidation was measured directly in the medium by the thiobarbituric acid reactive substances (TBARS) assay at 532 nm, using malondialdehyde (MDA) for the standard curve. Lipoprotein oxidation was also determined by the lipid peroxide test which analyzes lipid peroxide formation by their capacity to convert iodide to iodine, as measured spectrophotometrically at 365 nm.

Results

Demographics and Safety: Fifteen healthy male volunteers participated in the study. Subjects age range was 28 to 55 years (mean 42.1 years) and BMI range was 21.4 to 30 (mean 25.8). All subjects were tested negative to drugs and alcohol with no clinically significant abnormalities concerning laboratory parameters and vital sign measurements at screening and admission. No adverse events were observed or reported throughout the study.

Figure 9A:
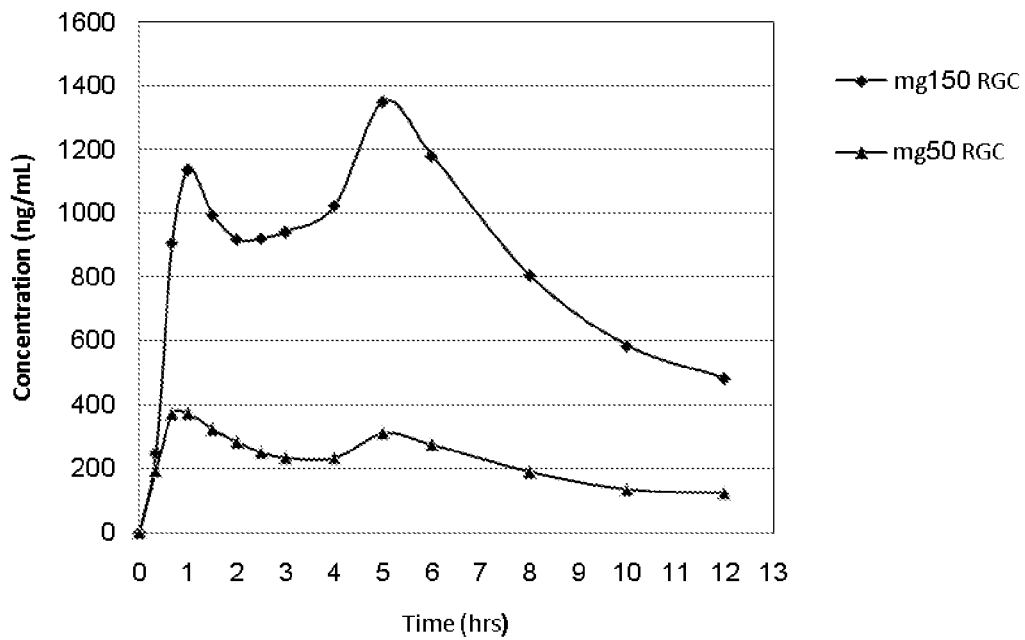
Figure 9B:
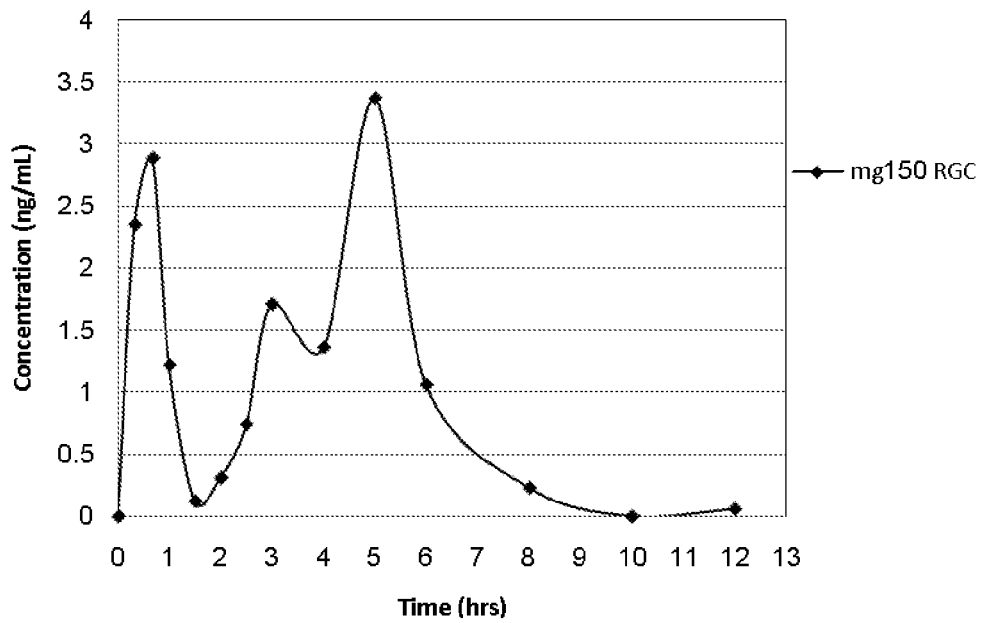

Plasma pharmacokinetics of free and total resveratrol: Mean trans-RGC-RES plasma concentration versus time curves for total RES and free RES is displayed in FIG. 9. As can be seen, RGC profile at both concentrations demonstrates two clear concentration peaks, the first after 1 hour and a second (higher) peak after 5 hours.

Mean pharmacokinetic parameters of t-RES are summarized in Tables 13A and 13B.

Tables 13A and 13B

| Plasma pharmacokinetic values following supplementation with RGC | | | |
|---|---|---|---|
| | Mean $AUC_t$ (ng · hr/ml) (% CV) | Mean $C_{max}$ (ng/ml) (% CV) | Median $T_{max}$ (hrs) [range] |
| A. Total resveratrol | | | |
| RGC 150 mg (n = 15) | 10404 (29.9) | 1684 (33.1) | 4.00 [0.67-6.00] |
| RGC 50 mg (n = 15) | 2694 (52) | 458.4 (52.4) | 1.00 [0.33-8.00] |
| B. Free resveratrol | | | |
| RGC 150 mg (n = 15) | 9.85 (74.3) | 6.89 (56.9) | 1 [0.33-4.00] |

Analyzing the first two time points of measurement, 0.33 and 0.67 hrs, reveals measurable quantities of RES in plasma of subjects received RGC (Table 14). Moreover, during the 0.33 hrs time point all subjects in the RGC groups (except one in the RGC 150 mg group) had measurable concentration of total RES (Tables 14 and 15).

TABLE 14

Subjects with detectable amounts of RES in plasma (total/free) during the first two time points of measurement.

| | Time point (hr) | | | |
|---|---|---|---|---|
| | 0.33 | | 0.67 | |
| | Total | Free | Total | Free |
| RGC 150 mg | 14/15 | 11/15 | 15/15 | 13/15 |
| RGC 50 mg | 15/15 | | 15/15 | |

TABLE 15

Concentration (ng/mL) of total and free RES at the first three time points of measurement after dosing.

| | Time point (hr) | | | | | |
|---|---|---|---|---|---|---|
| | 0.33 | | 0.67 | | 1 | |
| | Total | Free | Total | Free | Total | Free |
| RGC 150 mg | 248.9 ± 228 | 2.34 ± 3.5 | 906.6 ± 628 | 2.88 ± 2.5 | 1137 ± 640 | 1.21 ± 3.0 |

Conclusions

RES originated in RGC is characterized by the addition of one hexose moiety. Although the exact type of hexose and its precise location have not been identified it is most likely that RGC RES is piceid—the most common type of RES occurs naturally in red grapes. The phenomenon of two peaks demonstrated both in the free and total forms of RES is unique and has not been observed in other types of RES. It is possible that the presence of a glycoside group in RGC RES rendered it more soluble, as can be observed in the solubility test in which RGC-RES was more water soluble that synesthetic and plant derived sources of RES This unique two concentration peaks pattern may also attributed to the unique composition of RGC that contains a whole matrix of red grapes polyphenols and high level of glycoside resveratrol and the synergism between them, This trait may have found expression in the high rate of presence of RES in high concentration as fast as 20 minutes after administration.

As clearly seen in the concentration/time curve (FIG. 9A), RGC-RES yielded two very distinct concentration peaks appearing at 1 and 5 hours.

Importantly, concentration time curves of synthetic or yeast fermentation sources of RES (Poulson et al., 2013) as well as of plant derived RES (Amiot et al., 2013) show a distinct single concentration peak. This shows that one supplementation of RGC a day is enough for a prolonged effect, while in other products more than one supplementation or higher levels a day may be required for the same effect.

Example 7

Clinical Study—Effect of RGC Powder on Blood Pressure, Vascular Function and Plasma Oxidative Parameters in People Suffering from Prehypertension or Mild Hypertension A randomized, double-blind, placebo-controlled study was performed. Eligible subjects were enrolled and randomized into three treatment regimes, to receive 200 mg RGC powder, or 400 mg RGC powder or a placebo. No other relevant drugs were concomitantly taken by the treated subjects. The investigational product or placebo were ingested once daily for 12 weeks. The amounts of resveratrol and total polyphenols in the administered doses is presented in Table 16 below.

TABLE 16

Level of resveratrol and total polyphenols in RGC

| RGC (mg) | Resveratrol HPLC at 306 nm (mg) | Total polyphenols HPLC at 280 nm (mg) |
|---|---|---|
| 200 | 3 | 11.3 |
| 400 | 6 | 22.6 |

Results 46 subjects out of 55 (92%) completed the study. Baseline criteria were comparable across all treatment groups. The 200 mg group had higher BMI compared with the two other treatment groups. The mean age of the study population was 57.5±7.2 years (range: 41.7-70.0 years).

Safety

Treatment with RGC was safe and well tolerated. One serious adverse event, a heart burning that had turned into a chest ache was resolved simultaneously the next day and was considered moderate SAE unlikely related to the study product. All other adverse events were mild or moderate and were not considered related to the study product. No clinically significant changes in vital signs or laboratory values occurred during the study.

Efficacy

TABLE 17

Comparison of the effect of RGC on all outcome of measurements of 12 weeks of supplementation

| Parameter | RGC 200 mg | RGC 400 mg | Placebo |
|---|---|---|---|
| Systolic blood pressure, mmHg (N) | 126.7 ± 10.0 (9) | 133.6 ± 6.8 (17) | 134.3 ± 8.5 (15) |
| Change from baseline, mmHg (N) | −3.67 ± 8.96 (9) | 0.05 ± 9.40 (17) | −1.46 ± 6.47 (15) |
| Diastolic blood pressure, mmHg (N) | 78.3 ± 12.1 (9) | 84.3 ± 7.1 (17) | 82.8 ± 7.1 (15) |
| Change from baseline, mmHg (N) | −4.18 ± 8.96 (9) | 1.43 ± 8.02 (17) | 2.74 ± 5.30 (15) |
| Lipid peroxides (nmole/ml) (N) | 550.3 ± 41.5 (7) | 558.8 ± 32.5 (14) | 600.0 ± 48.3 (14) |
| Change from baseline (N) | −30.0 ± 48.2 (7) | −31.4 ± 56.0 (14) | 0.0 ± 51.9 (14) |

TABLE 17-continued

Comparison of the effect of RGC on all outcome of measurements of 12 weeks of supplementation

| Parameter | RGC 200 mg | RGC 400 mg | Placebo |
|---|---|---|---|
| FMD, % (N) | 6.96 ± 3.45 (5) | 3.59 ± 2.69 (8) | 4.74 ± 3.35 (9) |
| Change from baseline, % (N) | 1.96 ± 3.65 (6) | 2.14 ± 1.82 (8) | 0.21 ± 2.99 (9) |

*the numbers in the parentheses represent "N", which is the number of tested subjects Blood Pressure (BP)

Diastolic BP decreased in the RGC 200 mg group by −4.18±8.96 mm Hg. A comparison between the different groups showed that this change was statistically significantly different from placebo (Table 17, p=0.0320).

A Minor changes in the systolic BP, was observed between the baseline and the end of treatment in 200 mg treatment group (Table 17).

Plasma Oxidative Parameters

As shown in Table 17, treatment with RGC 400 mg significantly decreased lipid peroxide values by 31.4±56.0 (nmole/ml) between baseline and the end of treatment. A decrease in lipid peroxide values of 30.0±48.2 (nmole/ml) was also observed in the 200 mg treatment group.

Figure 10:
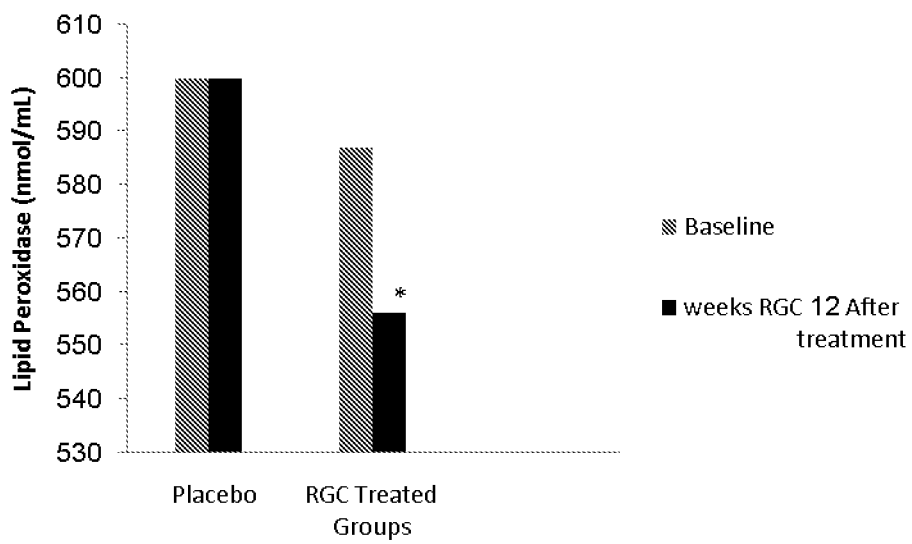
FIG. 10 presents the effect of RGC on plasma Lipid Peroxides in subjects after 12 weeks of RGC consumption (subjects administered with 200 mg and 400 mg RGC are jointly presented).

When the lipid peroxide values from the two RGC treatment groups were combined to allow a larger sample size, the mean lipid peroxide value decreased by 31.0±52.3 nmole/ml (FIG. 10, p=0.013).

Vascular Function Measured by Flow-Mediated Dilatation (FMD)

Vascular function was measured by FMD in six subjects from the 200 mg group, eight subjects from the 400 mg treatment group, and in nine subjects who received a placebo. A statistically significant increase of 2.14±1.82 mm Hg in FMD was observed in the RGC 400 mg group between baseline and the end of treatment (Table 17, p=0.013). FMD was performed by inflating a blood pressure cuff on the upper arm to 200 mm Hg for 5 minutes and then measuring the artery's dilation by ultrasonography at 60, 90 and 120 seconds after releasing the cuff.

Figure 11:
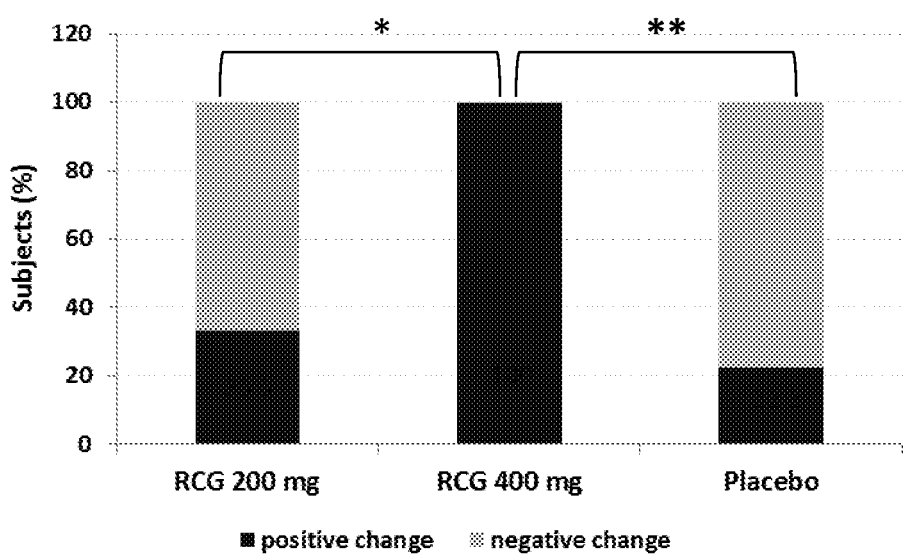
FIG. 11 presents the percent of subjects with relative positive change >70% in FMD values (*p<0.05, **p<0.005)

All eight subjects (100%) from the 400 mg treatment group experienced a positive relative change (>70% in FMD) compared to two out of six subjects (33.3%) from the 200 mg treatment group and two out of nine subjects (22.2%) who received a placebo (FIG. 11). The improvement rate observed in the RGC 400 mg group was statistically significantly different from that observed for both the 200 mg group and the placebo group (p=0.015 for 400 mg .vs. 200 mg and p=0.0023 for 400 mg .vs. placebo).

The results presented herein indicate that a daily consumption of RGC powder improves FMD and may improve oxidative stress in mild hypertensive subjects. RGC may also decrease diastolic and systolic blood pressure in subjects with moderate hypertension who are not medically treated.

Example 8

A Double-Blind, Randomized, Placebo Controlled Study of the Effect of Red Grape Cells (RGC) Powder Consumption on Measures of Healthy Moderately Trained Cyclists Experimental Procedure RGC cell culture powder was prepared according to example 1.

A clinical study was conducted on three groups of healthy moderately trained cyclists. 15 subjects received RGC at a dose of 200 mg per day and 14 subjects received RGC at a dose of 1000 mg per day for six weeks. 15 subjects (the control group) received placebo for six weeks.

At baseline visit before RGC consumption, the subjects underwent anthropometric measurements that included weight and height and body fat percentage measurements. Then the subjects underwent cardiopulmonary exercise testing using stationary cycle ergometer. Measured parameters included heart rate and blood pressure both at rest and at peak exercise as well as a set of aerobic fitness parameters. The exact measurements were repeated after 6 weeks of RGC or placebo consumption.

As can be seen in table 18, a significant 5%-6% decrease in resting diastolic blood pressure was seen only in the two RGC groups after supplementation. Similarly, there was also a lower mean resting systolic blood pressure. Measuring the number of subjects demonstrating a decrease in diastolic and systolic blood pressure revealed that nearly twice the number of such subjects in the both RGC groups as compared to placebo. Similar picture was revealed for resting heart rate.

At peak exercise (table 19), diastolic blood pressure was lower at study end in the low-dose group only, with borderline statistical significance. The number of participants that decreased the peak exercise diastolic blood pressure at study end was over three times higher in both RGC groups compared with the placebo group. Similar trend was observed for maximal systolic blood pressure measurements at peak.

Table 18 presents data on mean resting heart rate and blood pressure at baseline and at study end and their differences between groups. The proportion of participants that improved in each parameter is also presented in brackets.

| | Placebo | Low dose 200 mg per day | High dose 1000 mg per day | P value between changes |
|---|---|---|---|---|
| Resting heart rate | | | | |
| Baseline | 64 ± 10 | 66 ± 9 | 63 ± 11 | 0.59 |
| End | 64 ± 11 | 64 ± 9 | 58 ± 8 | |
| P value | 0.91 | 0.53 | 0.11 | |
| Resting heart rate, % decreased above 4 points | 8/15 (53%) | 10/15 (66%) | 10/14 (71%) | 0.57 |
| Systolic blood pressure | | | | |
| Baseline | 120 ± 12 | 123 ± 11 | 121 ± 11 | 0.20 |
| End | 121 ± 13 | 118 ± 12 | 118 ± 12 | |

-continued

|  | Placebo | Low dose 200 mg per day | High dose 1000 mg per day | P value between changes |
|---|---|---|---|---|
| P value | 0.62 | 0.16 | 0.25 |  |
| Systolic blood pressure, % decreased | 4/15 (26%) | 7/15 (46%) | 7/14 (50%) | 0.38 |
| Diastolic blood pressure |  |  |  |  |
| Baseline | 80 ± 9 | 81 ± 8 | 82 ± 6 | 0.19 |
| End | 79 ± 9 | 76 ± 9 | 78 ± 7 |  |
| P value | 0.64 | 0.01 | 0.02 |  |
| Diastolic blood pressure, % decreased | 5/15 (33%) | 8/15 (53%) | 7/14 (50%) | 0.50 |

Table 19 presents data on measures of maximal aerobic capacity at baseline and at study end and their differences between groups. The proportion of participants that improved in each parameter is also presented in brackets

|  | Placebo | Low dose 200 mg per day | High dose 1000 mg per day | P value between changes |
|---|---|---|---|---|
| Maximal systolic blood pressure |  |  |  |  |
| Baseline | 171 ± 26 | 180 ± 21 | 181 ± 15 | 0.58 |
| End | 179 ± 19 | 177 ± 19 | 183 ± 12 |  |
| P value | 0.15 | 0.95 | 0.60 |  |
| Maximal systolic blood pressure, % decreased | 4/15 (26%) | 6/15 (40%) | 6/14 (43%) | 0.62 |
| Maximal diastolic blood pressure |  |  |  |  |
| Baseline | 78 ± 6 | 79 ± 7 | 79 ± 6 | 0.24 |
| End | 78 ± 6 | 76 ± 9 | 77 ± 9 |  |
| P value | 0.92 | 0.09 | 0.46 |  |
| Maximal diastolic blood pressure, % decreased | 2/15 (13%) | 7/15 (46%) | 6/14 (43%) | 0.11 |
| Maximal load, watt |  |  |  |  |
| Baseline | 350 ± 55 | 335 ± 32 | 385 ± 52 | 0.67 |
| End | 347 ± 52 | 332 ± 49 | 391 ± 64 |  |
| P value | 0.56 | 0.56 | 0.56 |  |
| Maximal load, % increased | 4/15 (26%) | 3/15 (20%) | 5/14 (36%) | 0.64 |
| VO2max, ml/kg/min |  |  |  |  |
| Baseline | 48.9 ± 9.2 | 52.5 ± 7.9 | 53.5 ± 8.2 | 0.41 |
| End | 49.2 ± 9.6 | 52.2 ± 9.8 | 54.6 ± 9.7 |  |
| P value | 0.73 | 0.59 | 0.19 |  |
| VO2max, % increased | 8/15 (53%) | 5/15 (33%) | 8/14 (57%) | 0.38 |

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. A composition in a form of a powder comprising a cell line callus culture of fruit cells, grape berry cells, grown in vitro in a large scale up process, whereby the cell line callus culture of grape berry cells is derived from one or more of grape-berry cross section, grape-berry skin, grape-berry flesh, grape seed, grape embryo of seeded or seedless cultivars or grape seed coat; wherein the cell line callus culture of grape berry cells includes glycoside resveratrol in the form of piceid in an amount of at least 1000 mg/kg powder, and wherein the large scale up process includes preparing a liquid suspension of the cell line callus culture and wherein the cell line callus culture is grown in the liquid suspension in at least one bioreactor.

2. The composition of claim 1, characterized by two peaks of concentration of glycoside resveratrol in the form of piceid, in the plasma following a single administration of the composition.

3. The composition of claim 1, wherein the glycoside resveratrol is at least six fold more soluble than a synthetic resveratrol.

4. The composition according to claim 1, wherein the large scale up process comprises:
   growing fruit cells in a flask;
   inoculating the fruit cells from the flask into a first bioreactor;
   inoculating the fruit cells from the first bioreactor into another bioreactor, wherein the another bioreactor is a last bioreactor or an intermediate bioreactor and wherein at least one of the first and the another bioreactor is disposable; and
   harvesting the fruit cells from the last bioreactor;
   wherein the fruit cells harvested from the last bioreactor are dried.

5. The composition according to claim 4, wherein the fruit cells are grown in a Gamborg B5 medium.

6. The composition according to claim 5, wherein the Gamborg B5 medium is enriched with magnesium, phosphate or nitrate salts or a combination thereof.

7. The composition according to claim 5, wherein the Gamborg B5 medium is enriched with $KNO_3$, $MgSO_4$, $MgNO_3$ or $NaH_2PO_4$ or a combination thereof.

8. The composition according to claim 4, wherein the disposable bioreactor is made from one or more layers of polyethylene.

9. The composition according to claim 8, wherein the disposable bioreactor is made from an inner and outer layer of polyethylene and a middle nylon layer.

10. The composition according to claim 4, wherein the composition is administered once a day.

11. The composition according to claim 4, wherein the composition is a nutraceutical composition.

12. A composition in a form of a powder comprising a cell line callus culture of fruit cells, grape berry cells, grown in vitro in a large scale up process, whereby the cell line callus culture of grape berry cells is derived from one or more of grape-berry cross section, grape-berry skin, grape-berry flesh, grape seed, grape embryo of seeded or seedless cultivars or grape seed coat; wherein the cell line callus culture of grape berry cells includes glycoside resveratrol in an amount of at least 1000 mg/kg powder, wherein the large scale up process comprises:
   growing fruit cells in a flask;
   inoculating the fruit cells from the flask into a first bioreactor;
   inoculating the fruit cells from the first bioreactor into a second bioreactor, wherein the process comprises a last bioreactor, and the second bioreactor is the last bioreactor or an intermediate bioreactor and wherein at least one of the first and the second bioreactor is disposable; and harvesting the fruit cells from the last bioreactor;

wherein the fruit cells harvested from the last bioreactor are dried.

13. The composition according to claim 12, wherein the fruit cells are grown in a Gamborg B5 medium.

14. The composition according to claim 13, wherein the Gamborg B5 medium is enriched with magnesium, phosphate or nitrate salts or a combination thereof.

15. The composition according to claim 13, wherein the Gamborg B5 medium is enriched with $KNO_3$, $MgSO_4$, $MgNO_3$ or $NaH_2PO_4$ or a combination thereof.

16. The composition according to claim 12, wherein at least one disposable bioreactor is made from one or more layers of polyethylene.

17. The composition according to claim 16, wherein at least one disposable bioreactor is made from an inner and outer layer of polyethylene and a middle nylon layer.

18. The composition according to claim 12, wherein the composition is a nutraceutical composition.

19. The composition according to claim 18, wherein the composition is configured to be administered once a day.

* * * * *